United States Patent [19]

Mendelson

[11] Patent Number: 4,892,670

[45] Date of Patent: Jan. 9, 1990

[54] LUBRICATING COMPOSITIONS

[75] Inventor: Leah T. Mendelson, Santa Ana, Calif.

[73] Assignee: Union Oil Company of California, Los Angeles, Calif.

[21] Appl. No.: 695,958

[22] Filed: Jan. 29, 1985

[51] Int. Cl.$^4$ .......................................... C10M 141/02
[52] U.S. Cl. ..................... 252/37; 252/42.7; 252/46.4; 252/49.6; 252/56 R; 252/49.7
[58] Field of Search ................. 252/49.7, 42, 37, 42.7, 252/46.4, 49.6, 56 R, 47

[56] References Cited

U.S. PATENT DOCUMENTS

| | | | |
|---|---|---|---|
| 2,234,581 | 3/1941 | Rosen | 252/51 |
| 2,441,063 | 5/1948 | Gilmann | 260/404 |
| 2,999,064 | 9/1961 | Sluham | 252/34.7 |
| 3,000,925 | 9/1961 | Rudner et al. | 260/462 |
| 3,011,880 | 12/1961 | Liao et al. | 44/63 |
| 3,011,881 | 12/1961 | Emrick et al. | 44/63 |
| 3,030,405 | 4/1962 | Rudner et al. | 260/462 |
| 3,185,644 | 5/1965 | Knowles et al. | 252/33.6 |
| 3,186,946 | 6/1965 | Sluhan | 252/49.3 |
| 3,224,971 | 12/1965 | Knowles et al. | 252/46.3 |
| 3,227,739 | 1/1966 | Versteeg | 260/462 |
| 3,232,875 | 2/1966 | Abend | 252/49.6 |
| 3,256,310 | 6/1966 | Weil | 252/462 |
| 3,269,853 | 8/1966 | English et al. | 106/243 |
| 3,285,855 | 11/1966 | Dexter et al. | 252/57 |
| 3,313,727 | 4/1967 | Peeler | 252/18 |
| 3,321,506 | 5/1967 | Knowles et al. | 260/462 |
| 3,429,909 | 2/1969 | Schuster | 260/462 |
| 3,598,757 | 8/1971 | Cyba | 252/400 |
| 3,598,855 | 8/1971 | Cyba | 260/462 R |
| 3,642,652 | 2/1972 | Birgy | 252/389 |
| 3,692,681 | 9/1972 | Liston | 252/51.5 A |
| 3,697,574 | 10/1972 | Piasek et al. | 260/462 R |
| 3,755,388 | 8/1973 | Ludwig et al. | 260/404 |
| 3,764,593 | 10/1973 | Schuster | 260/97.5 |
| 3,912,643 | 10/1975 | Adams | 252/49.6 |
| 3,912,644 | 10/1975 | Adams | 252/49.6 |
| 3,929,652 | 12/1975 | Seni et al. | 252/46.7 |
| 3,977,986 | 8/1976 | Conte, Jr. et al. | 252/78.3 |
| 4,025,445 | 5/1977 | Hellmuth et al. | 252/49.6 |
| 4,032,304 | 6/1977 | Dorer, Jr. et al. | 44/70 |
| 4,115,286 | 9/1978 | Baldwin et al. | 252/46.3 |
| 4,136,039 | 1/1979 | Jager et al. | 252/8.8 |
| 4,176,076 | 11/1979 | Waldstein | 252/49.6 |
| 4,204,972 | 5/1980 | Knoblauch et al. | 252/78.1 |
| 4,226,734 | 10/1980 | Schuster | 252/49.3 |
| 4,234,435 | 11/1980 | Meinhardt et al. | 252/51.5 |
| 4,382,006 | 5/1983 | Horodysky | 252/49.6 |
| 4,400,284 | 8/1983 | Jessup et al. | 252/49.6 |
| 4,406,802 | 9/1983 | Horodysky et al. | 252/49.6 |
| 4,410,436 | 10/1983 | Holstedt et al. | 252/49.6 |
| 4,410,438 | 10/1983 | Horodysky | 252/49.6 |
| 4,412,928 | 11/1983 | Holstedt et al. | 252/49.6 |
| 4,427,560 | 1/1984 | Holstedt et al. | 252/49.7 |
| 4,431,552 | 2/1984 | Salentine | 252/46.7 |
| 4,474,670 | 10/1984 | Braid et al. | 252/32.7 |
| 4,478,732 | 10/1984 | Horodysky et al. | 252/49.6 |
| 4,490,265 | 12/1984 | Holstedt et al. | 252/49.7 |
| 4,492,640 | 1/1985 | Horodysky et al. | 252/46.3 |
| 4,492,642 | 1/1985 | Horodysky | 252/49.6 |
| 4,497,719 | 2/1985 | King et al. | 252/37 |
| 4,511,516 | 4/1985 | Holstedt et al. | 252/49.6 |
| 4,531,948 | 7/1985 | Knapp | 44/53 |
| 4,533,480 | 8/1985 | Holstedt et al. | 252/49.7 |
| 4,549,975 | 10/1985 | Horodysky | 252/49.6 |
| 4,557,843 | 12/1985 | Holstedt et al. | 252/46.4 |

FOREIGN PATENT DOCUMENTS

| 1306233 | 2/1973 | United Kingdom . |
| 1520743 | 8/1978 | United Kingdom . |
| 2177418A | 1/1987 | United Kingdom . |

*Primary Examiner*—Jacqueline V. Howard
*Attorney, Agent, or Firm*—Gregory F. Wirzbicki; Michael C. Schiffer

[57] ABSTRACT

A boron-containing heterocyclic compound prepared by reacting a primary amine or ammonia with an alkylene oxide or epoxide and then reacting concurrently or subsequently this reaction intermediate with a boric acid. This boron-containing heterocyclic compound may further be reacted with a metal, metaloid or other metal compound and even further contain sulfur, such as a sulfide group.

The boron-containing heterocyclic compound provides extreme pressure anti-wear properties when provided in a lubricating composition. The lubricating composition may also comprise anti-oxidants, copper corrosion inhibitors, and lead corrosion inhibitors. The anti-wear properties of a lubricating composition can be enhanced using the borates of the present invention in conjunction with a copper compound.

53 Claims, No Drawings

LUBRICATING COMPOSITIONS

TECHNICAL FIELD

This invention relates to lubricating oils and more particularly to improved lubricating oils containing additives, such as anti-wear and friction-reducing compounds, corrosion inhibitors and oxidation inhibitors.

BACKGROUND ART

It is well recognized in the petroleum industry that boron containing compounds are desirable additives for for lubricating oils. One such boron containing compound is disclosed in U.S. Pat. No. 3,224,971 to Knowles et al. which relates to intracomplexed borate esters and to lubricating compositions containing said esters. The borate esters are organo-boron compounds derived from boric acid and a bis (o-hydroxy-alkylphenyl) amine or sulfide.

Another extreme pressure lubrication composition is disclosed in U.S. Pat. No. 3,185,644 to Knowles et al., which relates to lubricating compositions containing amine salts of boron-containing compounds. The amine salts are formed by reaction of a hydroxy substituted amine and a trihydrocarbyl borate. The amine-borate compounds thus formed are described as useful as load carrying additives for mineral and synthetic base lubricating oils.

Boric-acid-alkylolamine reaction products and lubricating oils containing the same are disclosed in U.S. Pat. No. 3,227,739 to Versteeg. These amine type products are prepared by reacting equal molar proportions of diethanolamine or dipropanolamine and a long chain, 1, 2-epoxide. The intermediate reaction product thus produced is reacted with boric acid to produce the final reaction product. These compounds are added to lubricants to prevent rust formation.

Another boron ester composition is described in U.S. Pat. No. 3,269,853 to English et al. which discloses a boron ester curing agent which consists of a cyclic ring structure containing boron, oxygen, nitrogen, carbon and hydrogen.

Another boron composition is disclosed in U.S. Pat. No. 3,598,855 to Cyba which relates to cyclic borates of polymeric alkanolamines formed by reacting a borylating agent with a polymeric alkanolamine. The compounds thus formed are described as additives for a wide variety of petroleum products including lubricating oils.

Currently, there are phosphorus-containing additives which provide extreme pressure, anti-wear and/or friction-reducing properties to automotive engine oils. However, with the advent of the catalytic converter, alternative additives are needed. During combustion in an automotive engine, any oil which leaks or seeps into the combustion chamber yields phosphorus deposits which poison the catalyst in the catalytic converter. As a result, there is a need for automotive engine oil additives which are phosphorus-free but provide useful extreme pressure, anti-wear, and/or friction-reducing properties to the oil.

Accordingly, it is one object of the invention to provide a phosphorus-free additive having such properties and which, upon combustion, will not adversely affect the catalyst in the automotive catalytic converter.

It is yet another object of the present invention to provide boron-containing, heterocyclic compounds or derivatives thereof which have extreme pressure, anti-wear and friction-reducing properties.

Yet another object of the present invention is to provide a lubricating composition having extreme pressure, anti-wear and friction-reducing properties.

A further object of the present invention is to provide a lubricating composition containing extreme pressure, anti-wear, friction-reducing and corrosion prevention additives, and in addition, an anti-oxidant to prevent attack of oxidants upon metal bearings.

Other objects and advantages of the invention will be apparent from the following description.

SUMMARY OF THE INVENTION

This invention resides in certain boron-containing, heterocyclic compounds and derivatives of the same having the formula:

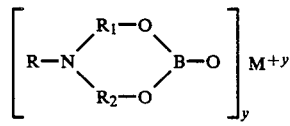

wherein R is an inorganic radical, or an organic radical having from 1 to about 50 carbon atoms, $R_1$ and $R_2$ are the same or different organic radicals having from 1 to about 50 carbon atoms, y is an integer from 1 to 4, and M is an organic or inorganic radical, and may, for example, be any metal, metalloid, or semi-metal, but preferably is either hydrogen or a transition metal having an atomic number of 21 through 30 or a Group IVA metal of the Periodic Table. (The Periodic Table referred to herein is located in the Handbook of Chemistry and Physics, 46th Edition). If M is an organic radical, it is preferred that it be chosen from the group consisting of alkyl, alkenyl, alkynyl, aryl, arylalkyl, and alkylaryl radicals of between 1 and 50 carbon atoms, with methyl and cyclohexyl radicals being among the most preferred groups.

The invention additionally resides in an extreme pressure, anti-wear and friction-reducing lubricating oil and a minor amount of a boron-containing, heterocyclic compound as above-described.

The boron-containing, heterocyclic compounds may conveniently be prepared by reacting either a saturated or unsaturated primary amine with an organic epoxide, such as an alkyl epoxide or an aromatic epoxide, to form a reaction product. The reaction product thus formed is reacted with boric acid to form a boron-containing, heterocyclic compound. Next, the boron-containing, heterocyclic compound may be reacted with either a salt of a metal, metalloid, or semi-metal to produce a metal derivative of the boron-containing, heterocyclic compound or with an alcohol to produce an ester-type derivative.

Alternatively, the boron-containing heterocyclic compounds may be produced by reacting either sulfur and/or a halogen and/or a sulfur halide with a boron-containing, heterocyclic compound containing unsaturateds in the R, $R_1$, $R_2$, and M radicals.

The above-described, boron-containing, heterocyclic compounds impart extreme pressure, anti-wear and friction-reducing properties to lubricating oils when added to said oils at use concentrations.

Another embodiment of the invention resides in a lubricating composition comprising a boron-containing, heterocyclic compound of the invention, and optionally any of (1) a polysulfide derivative of 2,5-dimercapto-1,3,4-thiodiazole, (2) terephthalic acid, and (3) either a bis(dithiobenzil) metal derivative, a sulfur bridged, bis(-hindered phenol) or an alkylated or dialkylated diphenyl amine or a mixture thereof.

In still another embodiment of the invention, a copper compound is used with a borate of the present invention in a lubricating compound. The copper compound enhances the anti-wear properties of such a composition.

DETAILED DESCRIPTION OF THE INVENTION

The present invention resides in extreme pressure, anti-wear and friction-reducing lubricating oil compositions comprising a major amount of an oil of lubricating viscosity and a minor amount of a boron-containing heterocyclic compound. Alternatively, corrosion inhibitors and anti-oxidants may be incorporated into the lubricating composition.

Anti-wear, friction-reducing and extreme pressure (or "E.P.") additives, as they are commonly called, are chemicals which are added to lubricating compositions to reduce friction and reduce or prevent destructive metal-to-metal contact in the lubrication of moving surfaces.

It has now been discovered that certain novel oil-soluble or dispersible boron-containing, heterocyclic compounds, when added to lubricating oils or grease, not only improve the ability of the lubricant to prevent seizure of the parts being lubricated (i.e., good E.P. properties) but in addition greatly reduce the amount of friction and wear of such moving parts.

The boron-containing, heterocyclic compounds described herein may be incorporated in a wide variety of lubricating oils, for example, mineral oil, crude oil, synthetic oil, industrial lubricating oils, cutting oil, metal working fluids and grease. Another use for the additive of the invention is in those fuels, e.g., certain aviation fuels and the like, wherein lubrication properties are desired. However, the most preferred use for the lubricating additive of the invention is in automotive engine oils. In this application, the boron-containing additives provide extreme pressure, anti-wear, and friction-reducing properties to the oil, and, upon combustion, prove innocuous to the conventional catalytic converter in modern automobiles.

If desired, the boron-containing, heterocyclic compounds described herein may be employed in conjunction with other additives commonly used in petroleum products. Thus, there may be added to the oil compositions of this invention rust and corrosion inhibitors, emulsifying agents, antioxidants or oxidation inhibitors, dyes, haze inhibitors, anti-static agents, detergents, dispersants, viscosity index improvement agents, pour point reducing agents, and other extreme pressure and anti-wear additives, such as the zinc dithiophosphate, triphenyl phosphorothionate, etc. Soaps or other thickening agents may be added to the lubricating oil compositions to form compositions having the consistency of a grease. When other additives are employed, it may be desirable, although not necessary, to prepare additive concentrates comprising concentrated solutions of the herein boron-containing, heterocyclic compounds together with said other additives whereby the several additives are added simultaneously. Dissolution of the additive or additive concentrate into the oil composition may be facilitated by mixing accompanied with mild heating, but this is not absolutely essential.

The herein-described boron-containing, heterocyclic compounds may be incorporated in the lubricating oils in any convenient way. Thus, boron-containing, heterocyclic compounds may be added directly to the oil by dissolving the desired boron derivative in the lubricating oil at the desired level of concentration.

Normally, the boron-containing, heterocyclic compound is blended with the lubricating oil such that its concentration is from about 0.1 to about 15 percent by weight, preferably from about 0.5 to about 10 percent by weight of the resultant oil composition. Alternatively, the compounds may first be blended with suitable solvents to form concentrates that may readily be dissolved in the appropriate oil at the desired concentration. If a concentrate is prepared, it is presently preferred that such concentrate comprise about 75 percent by weight of the compound, with the balance being a solvent. Suitable solvents which may be used for this purpose are naphtha, light mineral oil (i.e., 150 neutral to 450 neutral) and mixtures thereof. The particular solvent selected should, of course, be selected so as not to adversely affect the other desired properties of the ultimate oil composition.

The boron-containing, heterocyclic compounds of the present invention are represented generically by the following formula (I):

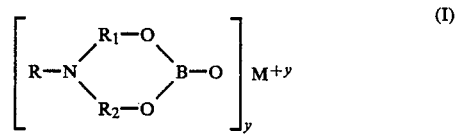

In the foregoing formula, R is an inorganic radical, e.g., hydrogen, chlorine, bromine, etc., or an organic radical having from about 1 to about 50 carbon atoms, typically about 1 to 30 carbon atoms, and preferably from about 1 to about 20 carbon atoms. Preferably, R is derived from aliphatic, alicyclic, or aromatic compounds. Most preferably, R is a substituted or unsubstituted hydrocarbyl group, particularly an alkyl, alkenyl, alkynyl, aryl, alkylaryl or arylalkyl radical having from about 1 to about 30 carbon atoms, preferably from about 1 to about 20 carbon atoms, especially from about 9 to about 20 carbon atoms. $R_1$ and $R_2$ are the same or different organic radicals bridging the nitrogen and oxygen atoms and have from about 1 to about 50 carbon atoms and preferably from about 2 to about 30 carbon atoms, with $R_1$ and $R_2$ oftentimes containing at least 3 or at least 4 carbon atoms. $R_1$ and $R_2$ are typically derived from aliphatic, alicyclic, or aromatic compounds and generally include at least two carbon atoms bridged between the nitrogen and oxygen atoms. Usually, $R_1$ and $R_2$ are the same or different substituted or unsubstituted hydrocarbyl or hydrocarbyloxy groups. Typical hydrocarbyl groups, which $R_1$ and $R_2$ may be, are substituted or unsubstituted alkylaryl, aryl, arylalkyl, alkyl, alkynyl, and alkenyl groups, with the most preferred radical bridging the oxygen and nitrogen atoms (in this and all embodiments hereinafter discussed with the exception of the embodiment typified by formula (IV) hereinafter) being an alkylaryl group wherein an ethylene radical bridges the oxygen and nitrogen atoms and an unsubstituted phenyl radical is bonded to the carbon closest to the oxygen atom, i.e.,

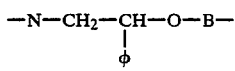

Typical hydrocarbyloxy groups which may bridge the nitrogen and oxygen atoms are those discussed hereinafter with respect to formula (IV). y is an integer from 1 to 4 and M is an organic or inorganic radical, but is usually either hydrogen or a metal, typically selected from the Groups IB, IIB, IIIB, IVB, VB, VIB, VIIB, VIII, IIIA, IVA, and VA of the Periodic Table, as found in the "Handbook of Chemistry and Physics," CRC Publishing Co., 46th Edition. Preferably, M is hydrogen or a transition metal having an atomic number from 21 to 30 or a Group IVA metal of the Periodic Table or mixtures thereof, and still more preferably copper. If M is an organic radical, it is typically of 1 to 50 carbon atoms and is derived from an aliphatic, alicyclic, or aromatic compound. Preferred radicals, when M is organic, are chosen from the group consisting of substituted and unsubstituted alkyl, alkynyl, alkenyl, aryl, arylalyl, and alkylaryl groups of between 1 and 50 carbon atoms, with methyl and cyclohexyl radicals being among the most preferred groups. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH₃ group. One of the most preferred substituted phenyl groups is the hindered phenyl group wherein the phenyl group is substituted at the 2 and 6 carbon atom of the phenyl ring with an organic group having more than 3 carbon atoms, e.g., the 2,6-di-tert-butyl phenyl groups, such as 4-methyl-2,6-di-tert-butyl phenyl. Hindered phenyl groups provide the compound with hydrolytic stability. It has also been unexpectedly found that non-hindered phenyl groups, whether substituted or unsubstituted, also provide the compound with hydrolytic stability.

(It should be noted herein that the terms "alkyl," "alkenyl," and "alkynyl" include cyclic species thereof, as well as the straight and branched chain species thereof. Also, for purposes of this invention, an "organic radical" is one which contains at least one carbon atom whereas an "inorganic radical" contains none. The term "inorganic radical," as used herein, is intended to include metals, semi-metals, and metalloids, as well as true inorganic radicals, e.g., —Cl, —Br, —I, —SO₃, and —H. The metals, semi-metals, and metalloids may be bonded ionically, covalently, or associatively.)

In one embodiment of the invention, useful when M is either hydrogen or a metal, but particularly when M is hydrogen, R is hydrogen or a substituted or unsubstituted hydrocarbyl group and at least one of R₁ and R₂, if both are aromatic, is other than an unsubstituted or alkyl substituted ortho-alkyl phenyl bridge, with the oxygen bonded at the ortho position relative to the alkyl group. Usually, if both R₁ and R₂ are aromatic, at least one contains no carbon atoms or three to five carbon atoms of the same aromatic ring in a chain of atoms bridging (or connecting) the oxygen atom to the nitrogen atom. Generally in this embodiment, R contains at least 9 carbon atoms if aliphatic and at least 7 carbon atoms if aromatic; further, R in this embodiment, and sometimes also R₁ and R₂, are organic radicals other than hydroxyhydrocarbyl groups, and particularly other than alkanol groups. Further still, it is preferred that at least one of R₁ and R₂ in this embodiment and even more preferably both are radicals other than an amino or hydrocarbylamino group, and it is further preferred that R₁ and R₂ contain only carbon atoms bridging the nitrogen and oxygen atoms, with none of said bridging carbon atoms being a member of an aromatic ring.

In a preferred embodiment, boron-containing, heterocyclic compounds of the present invention are of the following formula (II):

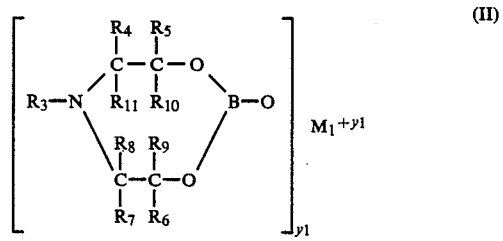

this formula, R₃ is hydrogen or an organic radical having from about 1 to about 30 carbon atoms, preferably from about 1 to about 20 carbon atoms. Most preferably, R₃ is hydrogen or a substituted or unsubstituted alkyl, alkenyl, alkynyl, aryl, alkylaryl or arylalkyl radical having from about 1 to about 30 carbon atoms, preferably from about 1 to about 20 carbon atoms. R₄, R₅, R₆ and R₇ are the same or different and are either an inorganic radical such as hydrogen or an organic radical, such as substituted or unsubstituted hydrocarbyl radicals having from 1 to about 50 carbon atoms, preferably from about 1 to 30 carbon atoms, wherein at least one (and preferably at least two) of the said R₄, R₅, R₆ or R₇ is an aryl, alkylaryl or arylalkyl radical having from about 6 to about 30 carbon atoms. R₈, R₉, R₁₀ and R₁₁ are the same or different radicals selected from hydrogen or organic radicals such as substituted or unsubstituted hydrocarbyl groups; typically, R₈, R₉, R₁₀ and R₁₁ are either hydrogen or an alkyl group having from about 1 to about 6 carbon atoms. y₁ is an integer from 1 to 4, and M₁ is an inorganic or organic radical, but is preferably selected from hydrogen or a metal, typically selected from a transition metal having an atomic number of 21 through 30 or a Group IVA metal. If M₁ is an organic radical, it is typically of 1 to 50 carbon atoms and is derived from an aliphatic, alicyclic, or aromatic compound. Preferred radicals, when M is organic, are chosen from the group consisting of substituted and unsubstituted alkyl, alkynyl, alkenyl, aryl, arylalkyl, and alkylaryl groups of 1 to 50 carbon atoms, with methyl and cyclohexyl radicals being among the most preferred. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH₃ group. One of the most preferred substituted phenyl groups is the hindered phenyl group wherein the phenyl group is substituted at the 2 and 6 carbon atom of the phenyl ring with an organic group having more than 3 carbon atoms, e.g., 2,6-di-tert-butyl phenyl groups, such as 4-methyl-2,6-di-tert-butyl phenyl. Hindered phenyl groups provide the compound with hydrolytic stability. It has also been unexpectedly found that non-hindered phenyl groups, whether substituted or unsubstituted, also provide the compound with hydrolytic stability.

In a preferred embodiment of the invention, $R_4$, $R_7$, $R_8$, $R_9$, $R_{10}$ and $R_{11}$ in formula (II) are hydrogen or substituted or unsubstituted alkyl groups, with hydrogen being especially preferred for all six radicals, and $R_5$ and $R_6$ are aromatic radicals, preferably such as alkylaryl, arylalkyl, or aryl radicals, but most preferably are both unsubstituted phenyl radicals. This embodiment of the invention, i.e., the embodiment containing aromatic radicals (and particularly unsubstituted phenyl radicals), has the added advantage of enhanced hydrolytic stability and solubility in lubricating oils.

The above-described, boron-containing, heterocyclic compounds are produced by (A) reacting a primary amine or ammonia with an alkylene oxide or epoxide or an aromatic oxide. The resulting product is then reacted with boric acid to give the corresponding boron-containing, heterocyclic compound. Primary amines useful in preparing the heterocyclic compounds of the present invention have the chemical formula $RNH_2$ wherein R is an organic or inorganic radical, preferably where R contains no more than 30 carbon atoms. Amines which are suitable for use herein include saturated amines such as methylamine, ethylamine, propylamine, butylamine, octadecylamine, dodecylamine, cyclohexylamine, phenylamine, cocoamine, and unsaturated amines such as tallowamine and oleylamine and mixtures thereof. The organic radical associated with such amines (e.g., the methyl group of methylamine, the ethyl group of ethylamine, etc.) will ultimately be the R group side chain emanating from the nitrogen atom of the heterocyclic borate of the invention. Thus, the R group side chain is determined by choice of amine, and if it is desired that R be inorganic rather than organic, then one may select ammonia to ensure that R is hydrogen, bromoamine to ensure that R is bromine, chloroamine to ensure that R is chlorine, hydroxylamine to ensure that R is an OH group, etc. However, since it is preferred in all embodiments of the invention that the R group side chain be organic in nature, the preferred amines for use in preparing the heterocyclic borates of the invention will be of formula $RNH_2$, wherein R is an organic radical.

A wide variety of alkylene oxides or epoxides may be used to prepare the precursor for the heterocyclic compounds herein. Typical alkylene oxides or epoxides which are suitable for use include ethylene oxide, propylene oxide, 1,2-epoxy-butane, cyclohexene oxide, cyclooctene oxide, and cyclododecene oxide, and mixtures thereof.

Generally, the primary amine (or ammonia) is reacted with an alkylene oxide or epoxide, optionally in the presence of a solvent, for example toluene, to produce a dialkoxylated amine. The primary amine and alkene oxide or epoxide are reacted at a molar ratio typically of about 1:2. If added, the solvent is introduced in sufficient quantity to dissolve or disperse the reactants. After the reaction proceeds to completion, the solvent is removed from the reaction product, for example, by evaporation, distillation, etc.

Next, the dialkoxylated amine is reacted with boric acid at a typical molar ratio of about 1:1, optionally in the presence of a solvent, for example, xylenes, benzene, toluene, etc., to produce the heterocyclic compound required herein. If used, the solvent will normally comprise from about 20 to about 50 weight percent, especially from about 30 to about 40 weight percent of the reaction mixture. The heterocyclic compound thus produced will contain from about 0.5 to about 10 weight percent, preferably from about 2 to about 5 weight percent of boron. The reactions herein are typically conducted under reflux at a temperature of from about 176° F. (80° C.) to about 392° F. (200° C.), especially from about 176° F. (80° C.) to about 300° F. (148.89° C.), at atmospheric pressure for about 1 to about 5 hours.

It is also possible to prepare a suitable heterocyclic compound herein from an aromatic oxide (or aromatic epoxides). Aromatic oxides (or aromatic epoxides) suitable for use herein preferably are of the following formula (III):

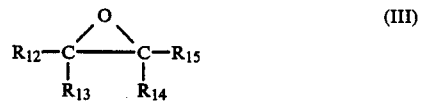

wherein at least one of said $R_{12}$, $R_{13}$, $R_{14}$ or $R_{15}$ is aryl, alkylaryl or arylalkyl with the remaining R groups being independently hydrogen or an organic radical having 1 to 30 carbon atoms, preferably hydrogen or an alkyl radical having 1 to 6 carbon atoms.

A wide variety of aromatic oxides may be used to prepare the epoxide/primary amine adducts needed to produce the boron compounds in the invention. Typical aromatic oxides for use herein include styrene oxide, alpha-methylstyrene oxide, para-tertiary-butylstyrene oxide, cresyl glycidyl ether, ortho-methylstyrene oxide, 1,2-epoxybenzene, and para-methyl styrene oxide and mixtures thereof. It should be noted that, of all the embodiments of the invention, the most highly preferred are those produced by borating the intermediate reaction product of a primary amine or ammonia with styrene oxide, with the resulting boron compound having a ring structure wherein ethylene groups connect the nitrogen and oxygen atoms of the ring and unsubstituted phenyl groups are attached to the carbon atom of said ethylene groups which are bonded to the oxygen atoms.

When an aromatic oxide is selected as a starting material, the primary amine may be reacted with the aromatic oxide in the presence of a solvent, for example, toluene, to produce an epoxide/amine adduct. The solvent is added in sufficient quantity to dissolve or disperse the reactants.

Generally, the primary amine and aromatic oxide are reacted at a pressure of from about atmospheric pressure to about 500 p.s.i.g. (35 atmospheres) at a temperature of from 176° F. (80° C.) to 392° F.(200° C.), for 1 to 5 hours. The primary amine is preferably reacted with the aromatic oxide at a molar ratio of 1:2 to produce an epoxide/amine adduct. It may be desirable to react the primary amine with two different aromatic oxides to produce a mixed epoxide/amine adduct. In this embodiment of the invention, one mole of the primary amine is reacted with one mole each of two different aromatic oxides to produce the desired tertiary amine. Yet another method of producing the desired epoxide/amine adduct involves reacting one mole of an aromatic-substituted alkene oxide and one mole of an alkene oxide, for example ethylene oxide, with a primary amine to produce an epoxide/amine adduct having an aromatic moiety and an alkyl moiety attached to the nitrogen atom.

Next, the epoxide/amine adduct is reacted with boric acid at a molar ratio of about 1:1, optionally in the presence of a solvent, for example, xylene, benzene, toluene, or the like, to produce a boron-containing, heterocyclic compound of the present invention. If a solvent is used, it will normally comprise from about 20 to about 50 weight percent, preferably from about 30 to about 40 weight percent of the reaction mixture. The reaction is conducted under reflux at a temperature of from 176° F. (80° C.) to 392° F. (200° C.), preferably from 176° F. (80° C.) to 300° F. (148.89° C.), at a pressure of from atmospheric pressure to about 500 p.s.i.g. (35 atmospheres), for about 1 to about 5 hours. The boron-containing heterocyclic compound thus produced will contain from about 0.5 to about 10 weight percent, preferably from about 2 to about 5 weight percent of boron.

Typical boron-containing, heterocyclic compounds herein which contain alkyl species in the heterocyclic ring structure are selected from the group consisting of methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate, tallowaminodiethylate hydrogen borate, dodecylamino di(-2-methylethylate) hydrogen borate, and dodecylamino di(-2-phenylethylate) hydrogen borate and mixtures thereof.

Representative boron-containing, heterocyclic compounds which contain alkylaryl species on the heterocyclic ring structure include the following compounds: 1-hydroxy- 3,7-diphenyl-5-dodecyl-5-aza-1-bora-2,8-dioxacyclooctane; 1-hydroxy-4,6-diphenyl-5-dodecyl-5-aza-1-bora-2,8-dioxacyclooctane; 1-hydroxy-4,7-diphenyl-5-dodecyl-5-aza-1-bora-2,8-dioxacyclooctane; 1-hydroxy-3,7-dicresyl-5-dodecyl-5-aza-1-bora-2,8-dioxacylooctane; 1-hydroxy-4,6-dicresyl-5-dodecyl-5-aza-1-bora-2,8-dioacyclooctane; 1-hydroxy-4,7-dicresyl-5-dodecyl-5-aza-1-bora-2,8-dioxacyclooctane; 1-hydroxy-3,7-dimethyl-3,7-diphenyl-5-dodecyl-5-aza-1-bora-2,8-dioxacyclooctane; 1-hydroxy-4,6-dimethyl-4,6-diphenyl-5-dodecyl-5-aza-1-bora-2,8-dioxacyclooctane; 1-hydroxy-4,7-dimethyl-4,7-diphenyl-5-dodecyl-5-aza-1-bora-2,8-dioxacyclooctane; 1-hydroxy-3, 7-para-tertiary-butyl-phenyl-5-dodecyl-5-aza-1-bora-2,8-dioxacyclooctane; 1-hydroxy-4,6-para-tertiary-butyl-phenyl-5-dodecyl-5-aza-1-bora-2,8-dioxacyclooctane; 1-hydroxy-4, 7-para-tertiary-butyl-phenyl-5-dodecyl-5-aza-1-bora-2,8-dioxacyclooctane; 1-hydroxy-3,7-diphenyl-5-coco-5-aza-1-bora-2,8-dioxacyclooctane; and 1-hydroxy-3,7-diphenyl-5-tallow-5-aza-1-bora-2,8-dioxacyclooctane and mixtures thereof. It should be noted that the methyl, ethyl, propyl, butyl, cyclohexyl, octadecyl, phenyl, steryl, oleyl, coco, tallow and the like moieties may be substituted for the dodecyl moiety in the above heterocyclic compounds.

Metal derivatives of the boron-containing, heterocyclic compounds herein are conveniently prepared by contacting the boron-containing, heterocyclic compound with a metal or metal compound, usually a metal in salt form. Thus, the metal acetates, propionates, etc., are suitable for use. The preferred metal compound for use in incorporating the metal ion into the borate of the invention is the metal acetate. Generally, the heterocyclic compounds are reacted with the metal compounds in a molar ratio range of from about 1:1 to about 6:1, preferably from about 1:1 to about 4:1, at a pressure of from about atmospheric to about 500 p.s.i.g. (35 atmospheres) and a temperature of from about 176° F. (80° C.) to about 392° F. (200° C.). Water and, in the case where metal acetates are used, acetic acid are then distilled from the reaction mixture using a water-cooled condenser. (It should be noted that not all metal salts are desirable for incorporating the metal ion into the boron-containing, heterocyclic compound. The metal carbonates, nitrates, chlorides, and sulfates, to name a few, are all undesirable as vehicles for imparting metal ions into the boron-containing, heterocyclic compound. These metal salts experience solubility problems and separation problems, and, in addition, undesirable ions frequently contaminate the boron-containing, heterocyclic compound.) Generally, the boron-containing, heterocyclic compounds are reacted with the metal compounds herein in a molar ratio range of from about 1:1 to about 6:1, especially from about 1:1 to about 4:1.

Desirable metals are usually selected from transition metals having an atomic number of 21 through 30 or Group IVA metals of the Periodic Table. Transition metals which are suitable for use are selected from scandium, titanium, vanadium, chromium, manganese, iron, cobalt, nickel, copper and zinc and mixtures thereof. Suitable Group IVA metals include lead and tin and mixtures thereof. Other metals (or metalloids or semimetals) may also be selected, such as gallium, bismuth, and antimony. Normally, the metal will comprise from about 1 to about 17 weight percent, preferably from about 5 to about 9 weight percent of the boron-containing, heterocyclic compound.

Representative metallic derivatives of the above compositions include the following compounds: copper di(1-oxy-3-,7-diphenyl-5-dodecyl-5-aza-1-bora-2,8-dioxacyclooctane); copper di-(1-oxy-4,6-diphenyl-5-dodecyl-5-aza-1-bora-2,8-dioxacyclooctane); copper di-(1-oxy-4,7-diphenyl-5-dodecyl-5-aza-1-bora-2,8-dioxacylooctane; copper di-(1-oxy-3,7-dicresyl-5-dodecyl-5-aza-1-bora-2,8dioxacyclooctane); copper di-(1-oxy-4,6-dicresyl-5-dodecyl-5-aza-1-bora-2,8-dioxacyclooctane); copper di-(1-oxy-4,7-dicresyl-5-dodecyl-5-aza-1-bora-2,8-dioxacyclooctane); copper di- (1-oxy-3,7-dimethyl-3,7-diphenyl-5-dodecyl-5-aza-1-bora-2,8-dioxacyclooctane); copper di-(1-oxy-4,6-dimethyl-4,6-diphenyl-5-dodecyl-5-aza-1-bora-2,8-dioxacyclooctane); copper di-(1-oxy-4,7-dimethyl-4,7-diphenyl-5-dodecyl-5-aza-1-bora-2,8-dioxacyclooctane); copper di-(1-oxy-3,7-para tertiary-butyl-phenyl-5-dodecyl-5-aza-1-bora-2,8-dioxacyclooctane); copper di-(1-oxy-4,6 para tertiary-butyl-phenyl-5-dodecyl-5-aza-1-bora-2,8-dioxacyclooctane); copper di-(1-oxy-4,7-para tertiary-butyl-phenyl-5-dodecyl-5-aza-1-bora-2,8-dioxacyclooctane); copper di-(1-oxy-3,7-diphenyl-5-coco-5-aza-1-bora-2,8-dioxacyclooctane); and copper di-(1-oxy-3,7-diphenyl-5-tallow-5-aza-1-bora-2,8-dioxacyclooctane). Other metals may be incorporated into the above compounds, i.e., substituted for the copper, for example, scandium, titanium, chromium, manganese, iron, cobalt, nickel, zinc, lead and tin and mixtures thereof. In addition, methyl, ethyl, propyl, butyl, cyclohexyl, octadecyl, phenyl, steryl, oleyl, coco, tallow and the like moieties may be substituted for the dodecyl moiety in the above-described heterocyclic compounds.

If it is desired that M in formula (I) hereinbefore, and also for the corresponding M radical of any of the borate of the invention formulas herein, be organic, then one may employ the following procedure: the borate of the invention is reacted under conditions as set forth hereinbefore with respect to preparing metal derivatives, but instead of using a metal salt, an alcohol of choice is employed and no water is added to the reaction. For example, if a methyl radical is desired for M, then methanol is employed; if a cyclohexyl radical, then cyclohexanol; and if an unsubstituted phenyl radical, then phenol. Optionally, a solvent such as toluene or xylene is also used. After the reaction is complete, water is removed by distillation, and the desired borate of the invention is obtained.

Another procedure, preferred especially for preparing borates of the invention with M as a substituted phenyl group, involves reacting the alcohol of choice e.g., 2,6-tert-butyl phenol, optionally in the presence of a solvent such as toluene or xylene, with boric acid in the presence of an acid catalyst, e.g., para-toluenesulfonic acid, or other organic soluble acids (e.g., acetic) or an ion exchange resin catalyst, Amberlyst 15, which is strongly acidic. The reaction may be accomplished by refluxing, which removes two moles of water for every mole of boric acid which reacts with the phenol compound. The resulting product, a boric acid:phenol adduct is in turn reacted with an amine:epoxide adduct, under conditions hereinbefore specified for reacting boric acid with an amine:epoxide adduct, and after water is removed by distillation, the final desired product is recovered.

Another species of the heterocyclic compounds herein are the bis(hydrocarbyloxy methylated) boron-containing, heterocyclic compounds. These compounds are of the following formula (IV):

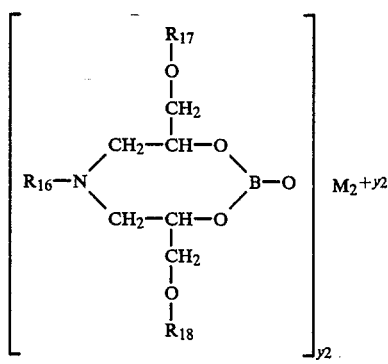
(IV)

where $R_{16}$ is an inorganic radical or an organic radical having from 1 to about 50 carbon atoms, $R_{17}$ and $R_{18}$ are the same or different organic radicals having from 1 to about 50 carbon atoms, $y_2$ is an integer from 1 to 4, and $M_2$ is an organic or inorganic radical but preferably is hydrogen or a metal, typically selected from a transition metal having an atomic number of 21 through 30 or a Group IVA metal as disclosed in the Periodic Table located in the Handbook of Chemistry and Physics, 46th Edition. If $M_2$ is an organic radical, it is preferred that it be chosen from the group consisting of substituted or unsubstituted alkyl, alkenyl, alkynyl, aryl, arylalkyl, and alkylaryl radicals having from 1 to 50 carbon atoms, with methyl and cyclohexyl radicals being among the most preferred groups. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH₃ group. One of the most preferred substituted phenyl groups is the hindered phenyl group wherein the phenyl group is substituted at the 2 and 6 carbon atom of the phenyl ring with an organic group having more than 3 carbon atoms, e.g., 2,6-di-tert-butyl phenyl groups, such as 4-methyl-2,6-di-tert-butyl phenyl. Hindered phenyl groups provide the compound with hydrolytic stability. It has also been unexpectedly found that non-hindered phenyl groups, whether substituted or unsubstituted, also provide the compound with hydrolytic stability.

When $R_{16}$, $R_{17}$ and $R_{18}$ are organic radicals, usually at least 65 percent, more usually at least 75 percent, and most usually at least 90 percent of the atoms composing said radicals will be carbon and hydrogen atoms. Preferably, $R_{16}$ is hydrogen or a substituted or unsubstituted alkyl, alkenyl, alkynyl, aryl, alkylaryl, or arylalkyl radica having from 1 to about 30 carbon atoms, and more preferably, from 1 to about 24 carbon atoms. On the other hand, $R_{17}$ and $R_{18}$ are preferably the same or different radicals selected from a substituted or unsubstituted alkyl, alkenyl, alkynyl, aryl, alkylaryl and arylalkyl radicals having from 1 to about 50 carbon atoms, and more preferably from 1 to about 30 carbon atoms, more preferably still from 1 to about 20 carbon atoms, and most preferably from 1 to about 10 carbon atoms.

In preparing the bis(hydrocarbyloxy methylated) boron-containing, heterocyclic compounds, a primary amine or ammonia (but preferably a primary amine) is reacted with an alkyl, aryl, alkylaryl or arylalkyl glycidyl ether to produce a bis(hydrocarbyloxy methylated) primary amine. Glycidyl ethers suitable for use herein preferably are of the following formula (V):

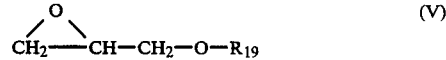
(V)

where $R_{19}$ is an organic radical having 1 to 50 carbon atoms with said organic radical in a preferred mode comprising at least 75 percent, preferably 90 percent of carbon and hydrogen atoms. Preferably, $R_{19}$ is a substituted or unsubstituted alkyl, aryl, alkylaryl or arylalkyl radical having from 1 to about 50 carbon atoms, preferably from 1 to about 30 carbon atoms, more preferably still from 1 to about 20 carbon atoms, and most preferably from 1 to about 10 carbon atoms.

A wide variety of glycidyl ethers may be used to prepare the oxylated primary amines needed to produce the heterocyclic compounds herein. Typical glycidyl ethers for use herein include methyl glycidyl ether, ethyl glycidyl ether, propyl glycidyl ether, butyl glycidyl ether, phenyl glycidyl ether, cresyl glycidyl ether, phenyl methyl glycidyl ether, ethyl phenyl glycidyl ether and phenyl ethyl glycidyl ether and mixtures thereof.

The primary amine may be reacted with the glycidyl ether in the presence of a solvent, for example, toluene to produce a dioxygenated amine. The solvent is added in sufficient quantity to dissolve or disperse the reactants.

Generally, the primary amine and glycidyl ether are reacted at a pressure of from about atmospheric pressure to about 500 p.s.i.g. (35 atmospheres) at a temperature of from 176° F. (80° C.) to 392° F. (200° C.) for 1 to 30 hour. The primary amine is preferably reacted with the glycidyl ether at a molar ratio of 1:2 to produce the bis(hydrocarbyloxy methylated) amine. It may be desirable to react the primary amine with two different glycidyl ethers to produce a mixed hydrocarbyloxy methylated amine. In this embodiment of the invention, one mole of the primary amine is reacted with one mole each of two different glycidyl ethers to produce the desired mixed hydrocarbyloxy methylated amine. Yet another method of producing the desired amine involves reacting one mole of an aromatic glycidyl ether and one mole of an alkyl glycidyl ether with a primary amine to produce an amine having an alkylaryl moiety and an alkyl moiety attached to the nitrogen atom of the amine.

Next, the bis(hydrocarbyloxy methylated) amine or mixed hydrocarbyloxy methylated amine is reacted with boric acid at a molar ratio of from about 1:1, optionally in the presence of a solvent, for example, xylene, benzene, toluene, or the like, to produce a bis(hydrocarbyloxy methylated) boron-containing, heterocyclic compound of the present invention. Normally, the solvent, if used, will comprise from about 20 to about 50 weight percent, preferably from about 30 to 40 weight percent of the reaction mixture. The reaction is conducted under reflux at a temperature of from 176° F. (80° C.) to 392° F. (200° C.), at a pressure of from atmospheric pressure to about 500 p.s.i.g. (35 atmospheres) for about 1 to about 30 hours. The compound thus produced will contain from about 0.5 to about 10 weight percent, preferably from about 2 to about 5 weight percent of boron.

In a preferred mode the primary amine and glycidyl ether are first reacted together and the intermediate reaction product thus produced is, next, reacted with boric acid.

An alternative method of producing the bis(hydrocarbyloxy methylated) boron-containing, heterocyclic compounds herein involves reacting the primary amine, glycidyl ether and boric acid in a one-step process.

Representative bis(hydrocarbyloxy methylated), boron-containing, heterocyclic compounds produced in accordance with the procedure herein include the following compounds: 1-hydroxy-3,7-di-(methoxymethyl)-5-dodecyl-5-aza-1-bora-2,8-dioxacyclooctane; 1-hydroxy-4,6-di-(methoxymethyl)-5-dodecyl-5-aza-1-bora-2,8-dioxacyclooctane; 1-hydroxy-3,7-di-(ethoxymethyl)-5-dodecyl-5-aza-1-bora-2,8-dioxacyclooctane; 1-hydroxy-3,7-di-(propoxymethyl)-5-dodecyl-5-aza-1-bora-2,8-dioxacyclooctane;1-hydroxy-4,6-di-(butoxymethyl)-5-dodecyl-5-aza-1-bora-2,8-dioxacyclooctane; 1-hydroxy-3,7-di-(methylphenoxymethyl)-5-dodecyl-5-aza-1-bora-2,8-dioxacyclooctane; 1-hydroxy-4,6-di-(methylphenoxymethyl)-5-dodecyl-5-aza-1-bora-2,8-dioxacyclooctane; 1-hydroxy-3,7-di-(ethylphenoxymethyl)-5-dodecyl-5-aza-1-bora-2,8-dioxacyclooctane; 1-hydroxy-4,6-di-(phenylmethoxymethyl)-5-dodecyl-5-aza-1-bora-2,8-dioxacyclooctane; and 1-hydroxy-3,7-di-(phenylethoxymethyl)-5-dodecyl-5-aza-1-bora-2,8-dioxacylooctane and mixtures thereof. It should be noted that the methyl, ethyl, propyl, butyl, cyclohexyl, octadecyl, phenyl, steryl, oleyl, coco and tallow moieties may be substituted for the dodecyl moiety in the above heterocyclic compounds. This embodiment of the invention has the added advantage of enhanced extreme pressure properties and a more pleasant odor.

Metal derivatives of the bis(hydrocarbyloxy methylated), boron-containing, heterocyclic compounds, herein are conveniently prepared by contacting the compound with a metal, usually in salt form. Thus, the metal acetates, proprionates, etc., are suitable for use. The preferred metal compound for use in incorporating the metal ion into the bis(hydrocarbyloxy methylated) boron-containing, heterocyclic compound is the metal acetate. Generally, these compounds are reacted with the metal compounds in a molar ratio range of from about 1:1 to about 6:1, preferably from about 1:1 to about 4:1, at a pressure of from about atmospheric to about 500 p.s.i.g. (35 atmospheres) and a temperature of from about 176° F. (80° C.) to about 392° F. (200° C.). Water and, in the case where metal acetates are used, acetic acid are distilled from the reaction mixture using a water-cooled condenser.

Representative of the metal compounds are: copper di[-1-oxy-2,7-di-(methoxymethyl)-5-dodecyl-5-aza-1-bora-2,8-dioxacyclooctane]; copper di-[1-oxy-4,6-di(-methoxymethyl)-5-dodecyl-5-aza-1-bora-2,8-dioxacyclooctane]; copper di-[1-oxy-3,7-di-(ethoxymethyl)-5-dodecyl-5-aza-1-bora-2,8-dioxacyclo-octane]; copper di-[1-oxy-3,7-di-(propoxymethyl)-5-dodecyl-5-aza-1-bora-2,8-dioxacyclooctane]; copper di-[1-oxy-4,6-di-(butoxymethyl)-5-dodecyl-5-aza-1-bora-2,8-dioxacyclooctane]; copper di-[1-oxy-3,7-di-(methylphenoxymethyl)-5-dodecyl-5-aza-1-bora-2,8-dioxacyclooctane]; copper di-[1-oxy-4,6-di-(methylphenoxymethyl)-5-dodecyl-5-aza-1-bora-2,8-dioxacyclooctane]; copper di-[1-oxy-3,7-di(ethylphenoxymethyl)-5-dodecyl-5-aza-1-bora-2,8-dioxacyclooctane]copper di-[1-oxy-4,6-di(-phenylmethoxymethyl)5-dodecyl-5-aza-1-bora-2,8-dioxacyclooctane]; and copper di-[1-oxy-3,7-di-(phenyl-ethoxymethyl)-5-dodecyl-5-aza-1-bora-2,-dioxacyclooctane] and mixtures thereof. Other metals may be incorporated into the above compounds, i.e., substituted for the copper, for example, scandium, titanium, vanadium, chromium, manganese, iron, cobalt, nickel, zinc, lead and tin and mixtures thereof. Semi-metals and metalloids may also be incorporated into such compounds. In addition, methyl, ethyl, propyl, butyl, cyclohexyl, octadecyl, phenyl, steryl, oleyl, coco and tallow moieties may be substituted for the dodecyl moiety in the above-described compounds.

It should be noted that the foregoing bis(hydrocarbyl methylated) boron-containing compounds of formula (IV) have been found to be soluble in 450 neutral oil, at least when prepared with tallowamine or cocoamine. However, the higher cost of preparing such compounds, particularly in comparison to compounds of formula (II) structure prepared with styrene oxide, makes the latter, i.e., the formula (II) compounds prepared from styrene oxide, a more preferred additive for automotive lubricating engines.

Also suitable herein are sulfohalogenated, boron-containing, heterocyclic compounds of the following formula (VI):

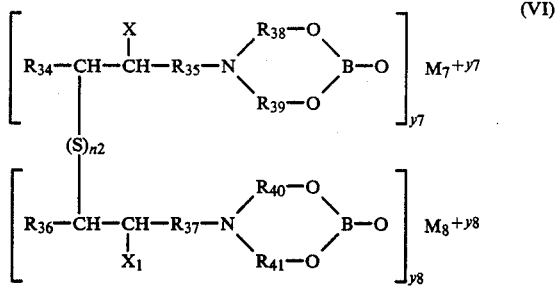

(VI)

wherein $R_{34}$ and $R_{36}$ may be the same or different organic or inorganic radicals but more typically $R_{34}$ and $R_{36}$ as well as $R_{35}$ and $R_{37}$ are the same or different organic radicals having from about 1 to about 30 carbon atoms, $R_{38}$, $R_{39}$, $R_{40}$ and $R_{41}$ are the same or different organic radicals having from about 1 to about 50 carbon atoms, $n_2$ is an integer from 1 to 4, preferably 1 or 2, X and $X_1$ are halogens independently selected from the group consisting of chlorine, fluorine, bromine and iodine and mixtures thereof, with chlorine being especially preferred. The radicals $R_{34}$, $R_{35}$, $R_{36}$ and $R_{37}$ are typically selected from the same or different, substituted or unsubstituted hydrocarbyl groups, such as, substituted or unsubstituted aliphatic and aromatic groups, particularly the alkyl, alkenyl, alkynyl, aryl, alkylaryl or arylalkyl radicals having from about 1 to about 30 carbon atoms, preferably from about 1 to about 20 carbon atoms. The organic radicals $R_{38}$, $R_{39}$, $R_{40}$ and $R_{41}$ are typically selected from the same or different, substituted or unsubstituted hydrocarbyl groups, such as, substituted or unsubstituted aliphatic and aromatic groups, particularly the alkyl, alkenyl, alkynyl, aryl, alkylaryl, or arylalkyl radicals having from about 1 to about 50 carbon atoms, preferably from about 1 to about 30 carbon atoms. Preferably $R_{38}$, $R_{39}$, $R_{40}$ and $R_{41}$ are alkylaryl or arylalkyl having from about 8 to about 30 carbon atoms. More preferably, $R_{38}$, $R_{39}$, $R_{40}$, and $R_{41}$ are alkylaryl groups and, most preferably, are alkylaryl groups wherein ethylene radicals connect the nitrogen and oxygen atoms and unsubstituted phenyl radicals are bonded to the carbon atoms of the ethylene radicals bonded to the oxygen atoms. $y_7$ and $y_8$ are the same or different integers from 1 to 4, and $M_7$ and $M_8$ may be an organic or inorganic group, but preferably are either hydrogen or a metal with the metal typically a transition metal having an atomic number from 21 to 30 or a Group IVA metal of the Periodic Table or mixtures thereof. If $M_7$ or $M_8$ is an organic radical, it is preferred that it be chosen from the group consisting of substituted and unsubstituted alkyl, alkenyl, alkynyl, aryl, arylalkyl, and alkylaryl radicals of between 1 and 50 carbon atoms, with methyl and cyclohexyl radicals being among the most preferred groups. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH$_3$ group. One of the most preferred substituted phenyl groups is the hindered phenyl group wherein the phenyl groups is substituted at the 2 and 6 carbon atom of the phenyl ring with an organic group having more than 3 carbon atoms, e.g., 2,6-di-tert-butyl phenyl groups, such as 4-methyl-2,6-di-tert-butyl phenyl. Hindered phenyl groups provide the compound with hydrolytic stability.

It has also been unexpectedly found that non-hindered phenyl groups, whether substituted or unsubstituted, also provide the compound with hydrolytic stability. $M_7$ and $M_8$ may be the same physical atom or species, e.g., the two borated radicals may be attached to the same metal atom or together may be one organic radical.

Halogenated, boron-containing, heterocyclic compounds useful in the present invention are of the following formula (VII):

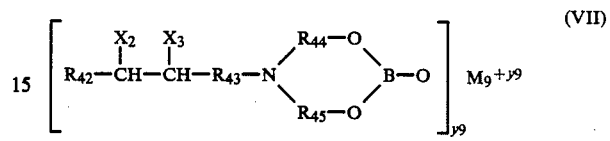

(VII)

wherein $R_{42}$ may be an inorganic radical but more typically $R_{42}$ and $R_{43}$ are the same or different organic radicals having from about 1 to about 30 carbon atoms, $R_{44}$ and $R_{45}$ are the same or different organic radicals having from about 1 to about 50 carbon atoms, $X_2$ and $X_3$ are halogens selected from the group consisting of chlorine, fluorine, bromine and iodine and mixtures thereof, with chlorine and bromine being especially preferred. The radicals $R_{42}$ and $R_{43}$ are typically selected from the same or different, substituted or unsubstituted hydrocarbyl groups, such as substituted or unsubstituted aliphatic and aromatic groups, particularly the alkyl, alkenyl, alkynyl, aryl, alkylaryl or arylalkyl radicals having from about 1 to about 30 carbon atoms, preferably from about 1 to about 20 carbon atoms. The organic radicals $R_{44}$ and $R_{45}$ are typically selected from the same or different, substituted or unsubstituted hydrocarbyl groups, such as, substituted or unsubstituted alihatic and aromatic groups, particularly the alkyl, aryl, alkylaryl or arylalkyl radicals having from about 1 to about 50 carbon atoms, preferably from about 1 to about 30 carbon atoms. Preferably, $R_{44}$ and $R_{45}$ are alkylaryl or arylalkyl having from about 8 to about 30 carbon atoms. More preferably, $R_{44}$ and $R_{45}$ are alkylaryl groups and, most preferably, are alkylaryl groups wherein ethylene radicals connect the nitrogen and oxygen atoms and unsubstituted phenyl radicals are bonded to the carbon atoms of the ethylene radicals bonded to the oxygen atoms. $y_9$ is an integer from 1 to 4, and $M_9$ may be an organic or inorganic group, but preferably is either hydrogen or a transition metal having an atomic number between 21 and 30 or a Group IVA metal of the Periodic Table and mixtures thereof. If $M_9$ is an organic radical, it is preferred that it be chosen from the group consisting of substituted and unsubstituted alkyl, alkenyl, alkynyl, aryl, arylalkyl, and alkylaryl radicals of between 1 and 50 carbon atoms, with methyl and cyclohexyl radical being among the most preferred groups. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH$_3$ group. One of the most preferred substituted phenyl groups is the hindered phenyl group wherein the phenyl group is substituted at the 2 and 6 carbon atom of the phenyl ring with an organic group having more than 3 carbon atoms, e.g., 2,6-di-tert-butyl phenyl groups, such as 4-methyl-2,6-di-tert-butyl phenyl. Hindered phenyl groups provide the compound with hydrolytic stability. It has also been unexpectedly found that non-hindered phenyl groups, whether substituted or unsubstituted, also provide the compound with hydrolytic stability.

Halogenated boron-containing, heterocyclic compounds typically include 1-hydroxy-3,7-diphenyl-5-(9-10-dichlorooctadecyl)-1-bora-2,8-dioxa-5-aza-cyclooctane; 1-hydroxy-3,7-diphenyl-5-(9-10-dichlorostearyl)-1-bora-2,8-dioxa-5-aza-cyclooctane; and 1-hydroxy-3,7-diphenyl-5-(dichlorotallow)-1-bora-2,8-dioxa-5-aza-cyclooctane and mixtures thereof. Other halogens which may be substituted for the chlorine above include fluorine, bromine and iodine and mixtures thereof.

Sulfurized forms of the borate of the invention are of the following formula (VIII):

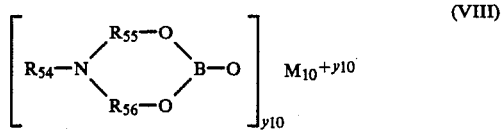

wherein $R_{54}$ is an inorganic or organic radical, $R_{55}$ and $R_{56}$ are the same or different organic radicals, and $M_{10}$ is an organic or inorganic radical, with $y_{10}$ being the valence of $M_{10}$, and preferably an integer from 1 to 4, further provided that at least one of $R_{54}$, $R_{55}$, $R_{56}$, and $M_{10}$ contains sulfur. Thus, for example, one or more of $R_{54}$, $R_{55}$, $R_{56}$, and $M_{10}$ may contain a "sulfide group," which is herein defined as sulfur bonded (1) as an end group as represented by a thio-group (—SH), (2) as part of the compound backbone (—CH$_x$—S—CH$_x$—), (3) as a pendant from the compound as represented by an episulfide group

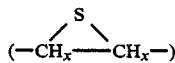

or (4) one or more sulfide or polysulfide bridges (—S— or —S$_{(n)}$—, wherein —S$_{(n)}$— represents two or more sulfur atoms bonded in series) connected to an organic radical, including another organic radical in formula (VIII) and an organic radical in a second borate of the invention of formula (VIII) structure or any of the borates of the invention previously illustrated by formula.

The preferred sulfurized borate of the invention contains a sulfide or polysulfide bridge connecting two borates of the invention, with the most preferred location of the bridge being between the two side R groups, i.e., as shown in the following formula (IX):

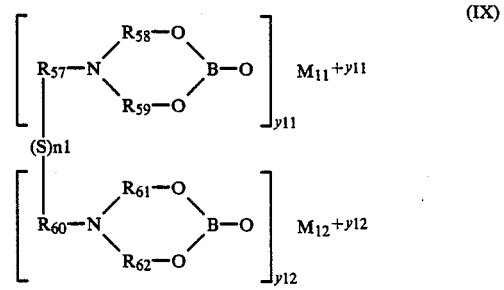

wherein all of the R groups are the same or different organic radicals and $M_{11}$ and $M_{12}$ are the same or different organic or inorganic radicals and (S)nl represents one or more sulfide or polysulfide bridges connecting $R_{57}$ and $R_{60}$.

As shown in formula (IX), one or more sulfur bridges exist between two borates of the invention. However, it is further contemplated in the invention that the sulfurized borate of the invention may have three or more borates of the invention, each of formula (VIII) structure wherein the R side groups (shown in formula (VIII) as $R_{54}$) and the M radicals of the borates of the invention may be the same or different inorganic or organic radicals and the R groups bridging the oxygen and nitrogen atoms (shown in formula (VIII) as $R_{55}$ and $R_{56}$) are the same or different organic radicals. It is most highly preferred that all sulfur bridges in the borate of the invention connect the R group side chains ($R_{54}$ in formula (VIII) and $R_{57}$ and $R_{60}$ in formula (IX)) emanating from the nitrogen atom of each borate of the invention, in which case the R group side chains would all be organic radicals. However, it is also contemplated in alternative embodiments that the sulfur bridge could connect elsewhere, e.g., from the R group side chain to M, from one R group connecting an oxygen and nitrogen atom to another, etc.

In formulas (VIII) and (IX), $R_{54}$, $R_{57}$, and $R_{60}$ are preferably organic radicals, usually having from 1 to 50 carbon atoms, and may, for example, be a substituted or unsubstituted hydrocarbyl group, particularly an alkyl, alkenyl, alkynyl, aryl, alkylaryl, or arylalkyl radical having from 1 to 30 carbon atoms, often from about 9 to 20 carbon atoms. $R_{55}$, $R_{56}$, $R_{58}$, $R_{59}$, $R_{61}$, and $R_{62}$ are generally organic radicals of 1 to 50 carbon atoms, and may, for example, be a substituted or unsubstituted hydrocarbyloxy group, e.g., the structure bridging the nitrogen and oxygen atom in formula (IV), or a hydrocarbyl group such as an alkyl, alkenyl, alkynyl, aryl, alkylaryl, or arylalkyl radical. Preferably, $R_{55}$, $R_{56}$, $R_{58}$, $R_{59}$, $R_{61}$, and $R_{62}$ are alkylaryl groups wherein ethylene radicals connect the nitrogen and oxygen atoms and unsubstituted phenyl radicals are bonded to the carbon atoms of the ethylene radicals bonded to the oxygen atom.

$M_{10}$, $M_{11}$, and $M_{12}$ are typically inorganic radicals such as hydrogen or a metal having an atomic number from 21 to 30, or a Group IVA metal. Other metals (or metalloids or semi-metals) may also be selected, such as gallium, bismuth, and antimony. $M_{10}$, $M_{11}$, and $M_{12}$ may also be organic radicals, preferably chosen from substituted or unsubstituted alkyl, alkenyl, alkynyl, aryl, arylalkyl, and alkylaryl radicals with methyl and cyclohexyl radicals being among the most preferred. Also among the most preferred groups, if M is organic, are substituted and unsubstituted phenyl groups, with substituted phenyl groups being particularly preferred. The phenyl group may be substituted with, for example, an acetyl group, a methyl radical, or an —O—CH$_3$ group. One of the most preferred substituted phenyl groups is the hindered phenyl group wherein the phenyl group is substituted at the 2 and 6 carbon atom of the phenyl ring with an organic group having more than 3 carbon atoms, e.g., 2,6-di-tert-butyl phenyl groups, such as 4-methyl-2,6-di-tert-butyl phenyl. Hindered phenyl groups provide the compound with hydrolytic stability. It has also been unexpectedly found that non-hindered phenyl groups, whether substituted or unsubstituted, also provide the compound with hydrolytic stability. Also, $M_{11}$ and $M_{12}$ may be the same physical atom or species, e.g., the two borate radicals may be attached or bonded to the same metal atom or together may be one organic radical.

One of the advantages of the sulfurized form of the borates of the invention is that of increased oxidation stability, as well as substantially enhanced extreme pressure properties. Generally, the sulfurized compounds exhibit the same or superior extreme pressure properties when used at weight percent concentrations substantially less than other heterocyclic, boron-containing compounds 30 disclosed herein.

The sulfurized, halogenated or sulfohalogenated compounds herein are produced in accordance with the procedure described before for producing the boron-containing, heterocyclic compounds with the added stipulation that the primary amine used to form the heterocyclic compound is unsaturated. Elemental sulfur is reacted with the heterocyclic compound in toluene, xylene, or the like to produce a sulfurized compound. The sulfohalogenated form of the compound may be produced by substituting a sulfur halide for the elemental sulfur above, for example, a sulfur chloride such as sulfur monochloride, sulfur dichloride, etc. The halogenated form of the heterocyclic compound is produced by substituting a halogen for the sulfur above.

The sulfurized compounds of the invention are preferably prepared by reacting one mole of sulfur with one equivalent of unsaturateds in the R side group of the boron heterocyclic compound or its metal derivative. For example, if 1-hydroxy-3,7-diphenyl-5-tallow-5-aza-1-bora-2,8-dioxacyclooctane is the chosen boron compound to be sulfurized, then 1 mole of sulfur is reacted with about 2.5 moles of the boron compound (because the boron compound contains about 0.40 equivalents of unsaturateds in the R group side chain). The reaction is conducted in the presence of a solvent such as toluene or xylene, using at least 3 moles of solvent for every mole of boron compound reacted. The reaction is conducted at elevated temperature with refluxing, with the time and temperature of reaction being dependent to a great extent upon the solvent chosen. If toluene, sulfurization is usually achieved in four hours at 110° C. under atmospheric pressure conditions; if xylene, then sulfurization is more rapid, occurring in 1 hour of refluxing at 137° to 140° C. under atmospheric pressure conditions. To prevent oxidation of the sulfur during said reactions, an inert gas blanket, such as nitrogen or argon, may be employed.

In an alternative embodiment of the invention, the elemental sulfur is first reacted with the unsaturated primary amine followed by subsequent reaction with the desired epoxide, which is in turn followed by reaction with boric acid. Alternatively still, an unsaturated amine:epoxide adduct may be produced first, followed by reaction with the elemental sulfur, which is in turn followed by reaction with boric acid. Reaction conditions for these embodiments typically are commensurate with those specified above for sulfurization reactions, reactions with boric acid, and reactions between amines and epoxides.

As stated above, the sulfurized versions of the borates of the invention typically form one or more sulfur bridges between R side groups emanating from the nitrogen atom. Such sulfur bridges, which may contain one sulfur atom or several in series, typically bond to carbon atoms immediately adjacent to a phenyl ring or alkenyl or alkynyl unsaturation. In other words, the sulfur bridge connects one R side group of a first borate of the invention with that of a second at locations formerly occupied by benzylic hydrogen (in the case of phenyl unsaturation) or an allylic hydrogen (in the case of alkenyl or alkynyl unsaturation). Thus, it will be understood that, by "unsaturateds" in the R side group, it is meant in the present specification and claims the number of allylic and benzylic hydrogens available in said R side group for substitution by a sulfur atom. And since the R side group originates in the primary amine, it will be understood that "unsaturated" in the term "unsaturated primary amine" refers to the number of allylic and benzylic hydrogens available in the R group of the amine (of formula $RNH_2$) for substitution by a sulfur atom.

(Of course, it will also be understood that, if the R groups connecting the nitrogen and oxygen atoms contain significant allylic and benzylic hydrogens, some bonding of sulfur atoms at such locations may also occur. But in the preferred embodiment, wherein styrene oxide is the epoxide chosen for reaction with the amine, and particularly when the phenyl groups of said styrene oxide ultimately are attached to the carbon atoms of the heterocyclic ring nearest the oxygen atoms, sulfur substitution is minimal, being impeded structurally by the ring itself and the influence of the oxygen atom.)

If desired, the sulfurization of the boron compound may be hastened by use of a vulcanization catalyst. The presently preferred catalyst is zinc bis(dibutylthiocarbamate), which is employed in the reaction mixture in a ratio to the boron compound of 0.01 to 0.50 moles for each mole of the boron compound.

The sulfohalogen compounds of the invention are prepared in a similar manner to the sulfurized versions, with the exception that no solvent is employed and, instead of sulfur as a reactant, a compound such as a sulfur monochloride ($S_2Cl_2$) is employed. The molar ratio of sulfur monochloride to boron compound is preferably the same as that for the sulfur to boron compound ratio employed in preparing the sulfurized species.

The halogenated species of the invention is typically prepared by introducing the boron compound to be halogenated, said boron compound containing an unsaturated R side group emanating from the nitrogen atom, into a 450 neutral oil or into a chlorinated hydrocarbon, e.g., carbon tetrachloride, followed by bubbling of chlorine or fluorine into the mixture at room temperature (25° C.). Generally, the bubbling takes place for about 15 minutes, but longer times are also suitable. If bromine is the desired halogen, it is added to the mixture in liquid form, in sufficient 30 amount to saturate a portion of or all the unsaturated sites of the R side group. Bromination of the boron compound can take place in as little as 10 minutes at 20° C. at atmospheric pressure. If iodine is the desired halogen, the procedure is modified by adding the iodine in sufficient quantity to saturate the unsaturated sites.

Sulfohalogenated, boron-containing, heterocyclic compounds include 10,10'-dithiodi[9-chloro-1-(5-hydroxy-3,7-diphenyl-1-aza-4,6-diocta-5-bora-cyclooctyl)-octadecane]; dithiodi[1-(5-hydroxy-3,7-diphenyl-1-aza-4,6-diocta-5-boracyclooctyl)-chlorotallow]; and dithiodi[1-(5-hydroxy-3,7-diphenyl-1-aza-4,6-diocta-5-bora-cyclooctyl)chlorosoya] and mixtures thereof. It should be noted that fluorine, bromine and iodine may be substituted for the chlorine above.

It will be noted in the foregoing descriptions related to the preparation of boron heterocyclic compounds of the invention that such descriptions relate to preparing the compounds with solvents present during both reactions, i.e., the reaction of a primary amine with an oxygen-containing organic compound followed by the reaction of the resulting intermediate product with boric acid, which yields the borated compound of the invention. However, the preferred embodiment of the invention as presently contemplated is that the borated compound of the invention be produced without any solvent being employed during these two reactions. (It is, however, preferred that, when preparing the sulfurized borated compounds previously described, the sulfurizing step using elemental sulfur be carried out in the presence of a solvent, e.g., toluene.) The reason that the absence of solvent is preferred is that it has been discovered that a more complete reaction to the desired borated product is accomplished when no solvent is employed. The presence of solvent tends to yield a mix of undesired and desired borates of the invention whereas the absence of solvent tends to selectively yield the desired borate of the invention.

The borates of the invention have, as stated previously, excellent extreme pressure, anti-wear, and friction-reducing properties. However, they have also been found to increase the corrosiveness of automotive lubricating engine oils, with the degree of corrosiveness depending on the purity of the borate of the invention employed, the amount employed, and the particular borate of the invention chosen. Some borates of the invention herein are less corrosive than others; for example, a borate of the invention of formula (I) structure hereinbefore, wherein $R_1$ and $R_2$ are ethylene groups, is more corrosive than the borate of the invention of formula (II) structure wherein $R_4$, $R_7$, $R_8$, $R_9$, $R_{10}$, and $R_{11}$ are hydrogen and $R_5$ and $R_6$ are both unsubstituted phenyl radicals. On the other hand, some of the sulfurized borate of the invention compounds described hereinbefore are significantly more corrosive than either of the aforementioned formulae (I) and (II) compounds, but this disadvantage is compensated for by the fact that only about one-half as much of the sulfurized compounds is needed to provide similar anti-wear, friction-reducing, and extreme pressure properties as said formulae (I) and (II) compounds.

In any event, if it is desired to lessen the corrosiveness of the borates of the invention, the lubricating oils into which they are added may be further provided with one or more corrosion inhibitors. Such corrosion inhibitors should impart lead and/or copper corrosion-inhibiting properties, and this because the bearings in automotive engines typically contain lead and/or copper.

In one embodiment of the present invention, copper corrosion in engine bearings is inhibited by adding to the lubrication composition a corrosion inhibiting amount, normally from 0.001 to about 5 weight percent, preferably from 0.005 to about 2.5 weight percent of a hydrocarbon polysulfide derivative of 2,5-dimercapto-1,3,4-thiadiazole having the formula (X):

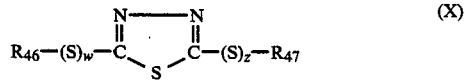

wherein $R_{46}$ and $R_{47}$ are the same or different moieties selected from hydrogen or straight or branched chain alkyl, cyclic or alicyclic alkyl, aryl, alkylaryl or arylalkyl radicals having from 2 to about 30 carbon atoms, and w and z are integers from 1 to 8. It should be noted that $R_{46}$ and $R_{47}$ cannot both be hydrogen because the compound would be rendered insoluble in lubricating oils. Thus, when R is hydrogen, $R_{47}$ must be selected from one of the other moieties described above, and vice versa.

Suitable among such compounds are polysulfides of 1,3,4-thiadiazole-2,5-bis(alkyl, di, tri or tetra sulfide) containing from 2 to about 30 carbon atoms. Desirable polysulfides include 1,3,4-thiadiazole-2,5-bis(octyldisulfide); 1,3,4-thiadiazole-2,5-bis(octyltrisulfide); 1,3,4-thiadiazole- 2,5-bis(octyltetrasulfide); 1,3,4-thiadiazole-2,5-bis(dodecyldisulfide); 1,3,4-thiadiazole-2,5-bis(-dodecyltrisulfide); 1,3,4-thiadiazole-2,5-bis(dodecyltetrasulfide); 2-lauryldithio-5-thioalphamethyl-styryl-1,3,4-thiadiazole; 2-lauryltrithio-5-thioalpha-methylstyryl-1,3,4-thiadiazole; 2-mercapto-5-octyldithio-1,3,4-thiadiazole and 2-mercapto-5-dodecyldithio-1,3,4-thiadiazole and mixtures thereof.

A small amount of terephthalic acid is effective as a lead corrosion inhibitor herein. The terephthalic acid may be prepared in accordance with conventional techniques and apparatus. Generally, the terephthalic acid is incorporated into lubricating oils at a concentration of from about 0.001 to about 1 weight percent, especially from about 0.005 to about 0.05 weight percent.

An oxidation inhibitor may also be employed in conjunction with the desired boron heterocyclic compound or in conjunction with the boron heterocyclic compound and corrosion inhibitors. Oxidation inhibitors are typically added to lubricating oils to prevent oxidative deterioration of organic materials. Any oxidation inhibitor known in the art may be employed, with suitable oxidation inhibitors being selected from the group consisting of bis(dithiobenzil) metal derivatives; sulfur bridged, bis(hindered phenols); and alkyl or diakyl, diphenylamines, dithiocarbamates and mixtures thereof. These compounds effectively limit or prevent the attack of oxidants on copper/lead metal. In addition, these compounds also help to control oil oxidation as manifested by reduced sludge and varnish formation, and by reduced oil thickening.

The bis(dithiobenzil) metal derivatives herein preferably have the formula (XI):

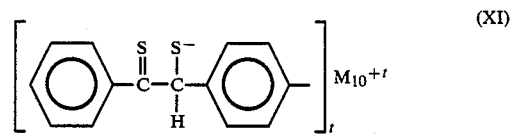

wherein $M_{10}$ is a first row transition metal and t is an integer from 1 to 4. Suitable transition metals include vanadium, chromium, manganese, iron, cobalt, nickel, copper, zinc, preferably iron, cobalt and nickel.

The bis(dithiobenzil) metal derivatives may be prepared, for example, by reacting benzoin with a phosphorus sulfide in the presence of dioxane at elevated temperature to produce the thiophosphoric ester of dithiobenzoin. The desired divalent metal, for example, metallic halide, is reacted with the above-described thiophosphoric ester of dithiobenzoin to produce the bis(dithiobenzil) metal derivative.

It should be noted that the bis(dithiobenzil) metal derivatives herein do not readily dissolve in lubricant compositions. However, when the bis(dithiobenzil) metal derivatives are mixed with the boron-containing, heterocyclic compounds herein, especially dodecylaminodi(phenylethylate) hydrogen borate, the mixture goes into solution in lubricant compositions such as motor oils.

The sulfur bridged, bis hindered phenols herein preferably have the formula (XII):

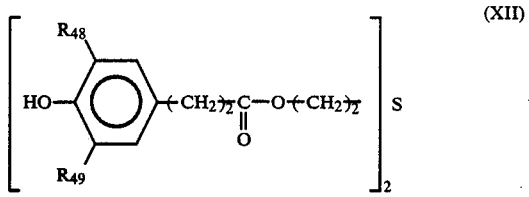

wherein $R_{48}$ and $R_{49}$ are selected from the same or different alkyl groups having from 1 to 6 carbon atoms.

Sulfur bridged, bis(hindered phenols) which are suitable for use as anti-oxidants include thiodiethyl bis(3,5-dimethyl-4-hydroxy) hydrocinnamate; thiodiethyl-bis(3,5-diethyl-4-hydroxy) hydrocinnamate; thiodiethyl bis(3,5-dipropyl-4-hydroxy) hydrocinnamate; thiodiethyl bis(3,5-dibutyl-4-hydroxy) hydrocinnamate; thiodiethyl bis(3,5-dipentyl-4-hydroxy) hydrocinnamate and thiodiethyl bis(3,5-dihexyl-4-hydroxy) hydrocinnamate and mixtures thereof.

One unexpected result in the present invention is that, when a sulfur-bridged, bis hindered phenol is employed as an oxidation inhibitor in the present invention, it further functions to reduce the corrosiveness of the boron compounds of the invention towards lead and copper automotive bearings. This discovery, which is illustrated hereinafter in Examples 54 to 60, permits one, through the introduction of a single additive, to take simultaneous advantage of two desirable properties—corrosion inhibition and oxidation inhibition.

Amines which are suitable for use as anti-oxidants or oxidation inhibitors herein have the formula (XIII):

wherein $R_{52}$ and $R_{53}$ are hydrogen or the same or different alkyl radicals having from about 1 to about 30 carbon atoms, preferably from about 1 to about 20 carbon atoms, with at least one of $R_{52}$ and $R_{53}$ being an alkyl group (mos preferably unsubstituted) having from about 1 to about 30 carbon atoms, e.g., 8 carbon atoms.

Generally, the anti-oxidants herein are incorporated into lubricant compositions at concentrations of from 0.01 to about 2 weight percent, preferably from 0.025 to about 0.10 weight percent, sometimes up to 1.0 weight percent.

It has also been found that the presence of copper compounds, dissolved in an automotive engine oil with borates of the invention, provides for enhanced antiwear properties. This embodiment of the invention allows for the use of less of the borate of the invention for the same level of desired antiwear protection. The preferred compounds for this use are copper carboxylates, such as copper naphthenate, in concentrations of about 100 to 125 wppm as Cu. However, even higher concentrations may be used, for example, up to about 3 percent by weight if desired.

This embodiment of the invention has an additional advantage in that copper carboxylates, such as copper naphthenate, has anti-oxidant properties. Other copper compounds also function in this manner, e.g., copper oleate. And in U.S. Pat. No. 4,122,033, herein incorporated by reference in its entirety, teachings are presented for employing copper compounds as anti-oxidants. Thus, the use of copper compounds having anti-oxidant properties functions in two ways in lubricating oils, first, as an anti-oxidant and, second, for enhancement of the anti-wear properties of the borate of the invention.

In addition to providing enhanced anti-wear properties, it has also been found that a lubrication oil comprising a borate of the invention, and particularly a sulfurized borate of the invention, with an oil-soluble copper compound exhibits anti-oxidant properties better than expected in comparison to the anti-oxidant properties of a lubrication oil comprising either the borate or copper compound alone.

The invention will be further described with reference to the following examples, which are intended to illustrate the invention, not to limit the claims.

EXAMPLE 1

A boron-containing, heterocyclic compound is prepared by adding 20 grams of boric acid, 95 grams of Armak Ethomeen C/12 [bis(2-hydroxyethyl) cocoamine] and 250 ml of toluene to a single-necked one liter round-bottomed flask. The toluene acts as a solvent and as an azeotrope for water produced during the reaction. It should be noted that boric acid is not soluble in toluene or Ethomeen C/12. The flask is placed in a heating mantle and fitted with a Dean-Stark trap that is topped with a condenser. The mixture thus formed is then heated until it begins to reflux. Next, the mantle is adjusted to give a moderate reflux rate. The reaction mixture is refluxed for one hour, or until the stoichiometric amount of water (12 ml.) collects in the Dean-Stark trap and all of the boric acid has dissolved, after which the toluene is distilled from the reaction product. The reaction product (103 grams) has a clear golden color and is a fluid liquid while hot but sets into a soft viscous material when cooled to room temperature. The compound is readily soluble in hydrocarbon solvents.

EXAMPLE 2

A boron-containing, heterocyclic compound is prepared by the following the procedure of Example 1 with the following substitution:

Armak Ethomeen T/12 [bis(2-hydroxyethyl) tallowamine] is substituted for the Armak Ethomee C/12. Substantially the same results are obtained.

EXAMPLE 3

A boron-containing, heterocyclic compound is prepared by mixing 20 grams of boric acid, 115 grams of Armak Ethomeen 18/12 [bis(2-hydroxyethyl) octadecylamine] and, as a solvent, 250 ml of toluene in a single-necked one liter round-bottomed flask. The flask is placed in a heating mantle and fitted with a Dean-Stark trap and water-cooled condenser. The mixture is heated under reflux for one hour, during which 12 ml of water collects in the Dean-Stark trap. The toluene is then distilled from the reaction product. The resulting compound is readily soluble in hydrocarbon solvents.

EXAMPLE 4

The procedure of Example 3 is followed to prepare a boron compound of the invention with the following exception: N,N-diethanol-n-methylamine (46.3 grams)

is substituted for the Armak Ethomeen 18/12. The reaction product thus produced is a liquid product with the consistency of honey when hot and becomes a waxy semi-solid when cooled to room temperature.

EXAMPLE 5

Boric acid (20 grams), N,N-diethanol-N-phenylamine (46.3 grams) and 250 mls of toluene are mixed in a one liter single-necked flask to prepare a boron-containing, heterocyclic compound. The flask is equipped with a heating mantle, Dean-Stark trap and water-cooled condenser. The mixture is heated under reflux until the reaction is completed (12 ml of water collects), approximately one hour, and the toluene is distilled from the reaction mixture. The product thus prepared is suitable for use an extreme pressure, antiwear and friction-reducing additive for lubrication compositions.

EXAMPLE 6

A metal derivative of the reaction product yielded in Example 1 is prepared by mixing 54 grams of the product of Example 1, 400 ml of toluene, 24.6 grams of nickel acetate and 150 ml of methanol in a single-necked, one liter round-bottomed flask which is equipped with a heating mantle and water-cooled condenser. The mixture is refluxed for four hours. Next, water, toluene, methanol and acetic acid are distilled from the reaction product. The product (59 grams) contained 7.8 weight percent nickel as determined by emission spectroscopy and the resulting product is a fluid green liquid when hot, which turns into a solid upon cooling to room temperature. The product is readily soluble in hydrocarbon solvents.

EXAMPLE 7

A metal derivative of the compound of Example 2 is prepared by mixing the reaction product of Example 2 (54 grams), 400 ml of toluene, 24 grams of nickel acetate and 150 mls of methanol in a single-necked, one-liter round-bottom flask, equipped with a heating mantle, Dean-Stark trap and water-cooled condenser. The mixture is refluxed for four hours and the toluene, water and acetic acid are distilled from the reaction product.

EXAMPLE 8

A zinc derivative of the reaction product of Example 1 is prepared by mixing 54 grams of said reaction product with 400 ml of toluene, 19.1 grams of zinc acetate and 50 ml of methanol in a single-necked, one-liter round-bottom flask, equipped with a heating mantle and water-cooled condenser. The mixture is refluxed for four hours and the toluene, methanol, water and acetic acid are distilled. The resulting product is suitable for use as an extreme pressure, anti-wear, friction-reducing additive for lubricating compositions.

EXAMPLE 9

Another metal derivative is prepared by following the procedure of Example 7 with the following exception: zinc acetate is substituted for the nickel acetate.

EXAMPLE 10

The extreme pressure, anti-wear and friction-reducing additives produced in Examples 1 and 6 in a 1:1 ratio mixture are mixed with 450 neutral oil and evaluated for performance. The additive mixture is mixed with the 450 neutral oil at 5 weight percent based on the total weight of the lubricant composition. This oil mixture is compared to Arco graphite lubricant and ASTM high reference oil, SAE 20W/30 for friction reduction and extreme pressure properties.

The lubricants are tested in accordance with the procedure disclosed in ASTM D3233-73 (Reapproved 1978) using a Falex lubricant tester. The test is performed by applying resistance to a revolving metal journal. Resistance is applied by two V-Blocks equipped with a ratchet mechanism which steadily increases pressure on the journal. The metal journal and V-Blocks are composed of steel in this example. The metal journal and V-Blocks are submerged in the lubricating composition to be tested. The results are indicated in the following Table 1:

TABLE 1

| | | LUBRICANT Torque on Journal lbs-in. (Newton-Meters) | | | |
|---|---|---|---|---|---|
| True Load Lbs. | (Newtons) | 450 Neutral Oil - No Additives | 450 Neutral Oil with 5 wt. % total of Examples 1 and 6 Compounds in a 1:1 ratio | Arco Graphite | ASTM SAE 20W/30 |
| 300 | (1,334) | 8 (0.904) | 4 (0.452) | 6 (0.678) | 6 (0.678) |
| 500 | (2,224) | 11 (1.243) | 6 (0.678) | 8 (0.904) | 7 (0.791) |
| 750 | (3,336) | 16 (1.808) | 9 (1.017) | 16 (1.808) | 12 (1.356) |
| 1,000 | (4,448) | Journal Shear | 14 (1.582) | 21 (2.373) | 20 (2.260) |
| 1,250 | (5,560) | — | 21 (2.373) | 26 (2.937) | 24 (2.712) |
| 1,500 | (6,672) | — | Journal Shear | Journal Shear | Journal Shear |

It should be noted that substantially the same results are obtained when the nickel derivative of Example is substituted for the nickel derivative of Example 6.

EXAMPLE 11

The lubricant of Example 10 containing the two compounds of the invention is tested in accordance with the procedure set forth in Example 10 with the following exception: the metal journal and V-Blocks are constructed from cast iron. The results are indicated in the following Table 2:

TABLE 2

| | | LUBRICANT Torque on Journal lbs-in. (Newton-Meters) | | |
|---|---|---|---|---|
| True Load Lbs. | (Newtons) | 450 Neutral Oil with 5 wt. % total of Examples 1 and 6 Compounds in a 1:1 ratio | Arco Graphite | ASTM SAE 20W/30 |
| 300 | (1,334) | 3 (0.339) | 6 (0.678) | 6 (0.678) |
| 500 | (2,224) | 4 (0.452) | 7 (0.791) | 7 (0.791) |
| 750 | (3,336) | 7 (0.791) | 13 (1.469) | 10 (1.130) |
| 1,000 | (4,448) | 12 (1.356) | 15 (1.695) | 14 (1.582) |
| 1,250 | (5,560) | 14 (1.582) | 17 (1.921) | 17 (1.921) |
| 1,500 | (6,672) | 16 (1.808) | 20 (2.260) | 19 (2.146) |
| 1,750 | (7,784) | 18 (2.034) | 23 (2.599) | 21 (2.373) |
| 2,000 | (8,896) | Journal Wear | 24 (2.712) | Journal Wear |
| 2,250 | (10,008) | — | Journal Wear | — |

The nickel derivative of Example 7 may conveniently be substituted for the nickel derivative of Example with substantially the same results.

EXAMPLE 12

The lubricant of Example 10 containing the two compounds of the invention is tested in accordance with the procedure set forth in Example 10 with the following exception: the journal is constructed from cast iron and the V-Blocks are constructed from chrome. The lubricant properties are compared with those of Arco graphite and ASTM, SAE 20W/30 lubricants. The lubricant compositions are tested in accordance with the procedure disclosed in ASTM:D3233-73 (Reapproved 1978) using a Falex lubricant tester. The results are indicated in the following Table 3:

TABLE 3

| | LUBRICANT Torque on Journal lbs-in. (Newton-Meters) | | |
|---|---|---|---|
| True Load Lbs. (Newtons) | 450 Neutral Oil with 5 wt. % total of Examples 1 and 6 Compounds in a 1:1 ratio | Arco Graphite | ASTM SAE 20W/30 |
| 300 (1,334) | 5 (0.565) | 4 (0.452) | 5 (0.565) |
| 500 (2,224) | 6 (0.678) | 5 (0.565) | 7 (0.791) |
| 750 (3,336) | 7 (0.791) | 8 (0.904) | 10 (1.130) |
| 1,000 (4,448) | 12 (1.356) | 11 (1.243) | 14 (1.582) |
| 1,250 (5,560) | 15 (1.695) | 16 (1.808) | 20 (2.260) |
| 1,500 (6,672) | Journal Wear | Journal Wear | Journal Wear |

EXAMPLE 13

An extreme pressure, anti-wear and friction reducing lubricant composition is prepared by mixing 5 weight percent of the zinc additive of Example 8 with 450 neutral oil. The lubricant composition reduces wear and friction of metal components in moving contact with each other and, in addition, lubricates said metal surfaces under extreme pressure or boundary lubrication conditions.

EXAMPLE 14

The zinc derivative additive of Example 9 is admixed with 450 neutral oil at 5 percent by weight based upon the total lubricant composition to prepare an extreme pressure, anti-wear and friction-reducing lubricant composition. The zinc derivative additive imparts extreme pressure, anti-wear and friction-reducing properties to the 450 neutral, lubricating oil.

EXAMPLE 15

A lubricant composition containing the nickel heterocyclic compound of Example 6 and 450 neutral oil is tested for extreme pressure, anti-wear and friction-reducing properties in a 1973 Chevrolet 350 cu. in. displacement V-8 engine which is run continuously for 196 hours on a single fill of the lubricating composition. The lubricating oil does not contain conventional zinc dialkydithiophosphate anti-wear additives. The lubricant composition is disclosed in detail in the following Table 4:

TABLE 4

| Compound | Weight Percent |
|---|---|
| 450 neutral oil | 89.945 |
| Example 1 Compound | 2.500 |
| Nickel Compound of Example 6 | 2.500 |
| Oronite OLOA 1200[A] | 4.000 |
| Chlorowax 40[B] | 1.000 |

TABLE 4-continued

| Compound | Weight Percent |
|---|---|
| UNAD 242[C] | 0.010 |
| Terephthalic Acid[D] | 0.025 |
| Quinizarin[E] | 0.020 |

[A] Oronite OLOA 1200 - alkyl succinimide type ashless dispersant.
[B] Chlorowax 40 - Chlorinated paraffin containing 40% chlorine.
[C] UNAD 242 - Silicone type defoamant with kerosene.
[D] Terephthalic acid - Corrosion inhibitor.
[E] Quinizarin - Antioxidant.

The Chevrolet engine is programmed to run in a repeating cycle that averaged approximately 40 MPH. The cycle is disclosed in the following Table 5:

TABLE 5

| Cycle | RPM | Speed MPH (Kilometers/Hr.) | Time(MIN.) |
|---|---|---|---|
| 1 | 700 | 0 (0) | 2.0 |
| 2 | 1,700 | 45 (72.4) | 3.0 |
| 3 | 1,200 | 30 (48.3) | 4.0 |
| 4 | 2,225 | 60 (96.5) | 0.12 |
| 5 | 2,400 | 65 (104.6) | 3.0 |

After the 196 hour engine test is completed, several areas in the engine which are subject to wear are closely examined. These areas include: main bearings, top end bearings, cam shaft bearings, valve lifters and cam shaft lobes.

The length of the engine run is equivalent to approximately 8,000 miles of driving. A detailed examination of the above-described components indicated no abnormal or excessive wear.

EXAMPLE 16

The extreme pressure, anti-wear and friction-reducing additives of Example 1 and Example 2 are individually mixed with SAE 10W/40 motor oil containing 0.15 weight percent of phosphorus and 0.17 weight percent of zinc. In addition, the motor oil contains 0.21 weight percent of calcium.

The resulting lubricant compositions are tested in accordance with the procedure disclosed in ASTM D3233-73 (Reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. The results are set forth in the following Table 6:

TABLE 6

| | Torque on Journal,lb.-in (Newtons-Meters) | | |
|---|---|---|---|
| True Load lbs (Newtons) | SAE 10W/40[a] Without Additive | SAE 10W/40[a] Plus 1 wt. % of Ex.1 Compound | SAE 10W/40[a] Plus 1 wt. % of Ex.2 Compound |
| 100 (445) | 8 (0.904) | 7½ (0.847) | 7½ (0.847) |
| 250 (1,112) | 12 (1.356) | 10 (1.130) | 9 (1.017) |
| 500 (2,224) | 19 (2.147) | 15 (1.695) | 14 (1.582) |
| 750 (3,336) | 22 (2.486) | 18 (2.034) | 19 (2.146) |
| 1,000 (4,448) | 25 (2.825) | 22 (2.486) | 22 (2.486) |
| 1,250 (5,560) | 35 (3.954) | 25 (2.825) | 25 (2.825) |
| 1,500 (6,672) | Journal Shear | 27 (3.050) | 27 (3.050) |
| 1,750 (7,784) | — | Journal Shear | 33 (3.728) |
| 2,250 (10,008) | — | — | Journal Shear |

[a] Union Super Motor Oil, marketed commercially by the Union Oil Company of California.

EXAMPLE 17

A metal heterocyclic compound is prepared by following the procedure of Example 6 with the following changes: 31 grams of reaction product yielded in Example 1 is mixed with 19 grams of lead (II) acetate, 150 ml. of toluene and 25 ml of methanol. The mixture is refluxed for 2 hours, after which, the toluene, methanol, water and acetic acid (produced from acetate) are distilled using conventional techniques and apparatus. The resulting lead-containing product (32.6 grams) is a golden colored oil with the consistency of honey.

EXAMPLE 18

The extreme pressure, anti-wear and friction-reducing additive, lead derivative produced in accordance with the procedure of Example 17 is blended with 450 neutral oil at 5 percent by weight based on the total weight of the lubricant composition. The above lubricant composition is compared to Arco graphite lubricant and ASTM high reference oil, SAE 20W-30 for friction reduction and extreme pressure properties.

The lead derivative and 450 neutral oil mixture is compared to Arco graphite and ASTM, SAE 20W/30 in accordance with the procedure disclosed in ASTM:D3233-73 (Reapproved 1978) using a Falex lubricant tester. The test is performed by applying resistance to a revolving metal journal. Resistance is applied by two V-Blocks equipped with a ratchet mechanism which steadily increases pressure on the journal. The metal journal and V-Blocks are composed of steel in this example. The metal journal and V-Blocks are submerged in the lubricating composition to be tested. The results are indicated in the following Table 7:

TABLE 7

| | Torque on Journal lbs-in. (Newton-Meters) | | |
|---|---|---|---|
| True Load Lbs. (Newtons) | 450 Neutral Oil with Lead Derivative | Arco Graphite | ASTM SAE 20W/30 |
| 300 (1,334) | 7 (0.791) | 6 (0.678) | 6 (0.678) |
| 500 (2,224) | 11 (1.243) | 8 (0.904) | 7 (0.791) |
| 750 (3,336) | 14 (1.582) | 16 (1.808) | 12 (1.356) |
| 1,000 (4,448) | 20 (2.260) | 21 (2.373) | 20 (2.260) |
| 1,250 (5,560) | 23 (2.599) | 26 (2.937) | 24 (2.712) |
| 1,500 (6,672) | 40 (4.520) | Journal Shear | Journal Shear |
| 1,750 (7,784) | 85 (9.605) | | |
| 2,000 (8,896) | 94 (10.622) | | |
| 2,250 (10,000) | 90 (10.170) | | |
| 2,500 (11,120) | 71 (8.023) | | |
| 2,750 (12,232) | 79 (8.927) | | |
| 3,000 (13,344) | 70 (7.345) | | |
| 3,250 (14,456) | 70 (7.345) | | |
| Stopped due to inability to increase load. | | | |

EXAMPLE 19

A copper-heterocyclic compound is prepared by adding 62 grams of the boron-containing, heterocyclic reaction product yielded in Example 1, 150 ml of toluene, ml of water and 18.2 grams of cupric acetate to a 500 ml., single-necked round-bottom flask equipped with a Dean-Stark trap and condenser. The mixture is refluxed for 8 hours, after which, water, toluene and produced acetic acid (from acetate) are distilled leaving 68 grams of a green solid.

EXAMPLE 20

The copper derivative additive produced in Example 19 is admixed with 450 neutral oil at 5 weight percent based on the total weight of the lubricant composition and evaluated for performance in accordance with the procedure of Example 18 with the following exception: the lubricant properties of the copper derivative-450 neutral oil mixture are compared with those of 450 neutral oil and SAE 10W/40 lubricants. The results are indicated in the following Table 8:

TABLE 8

| | Torque on Journal lbs.-in (Newton-Meters) | | |
|---|---|---|---|
| True Load lbs. (Newtons) | 450 Neutral Oil with Copper Compound from Ex. 19 | 450 Neutral Oil Without Additive | SAE 10W-40 |
| 300 (1,334) | 9 (1.017) | 10 (1.130) | — |
| 500 (2,224) | 11 (1.243) | 15 (1.695) | 17 (1.921) |
| 750 (3,336) | 17 (1.921) | 23 (2.599) | 21 (2.373) |
| 1,000 (4,448) | 20 (2.260) | Journal Shear | 28 (3.163) |
| 1,250 (5,560) | 28 (3.163) | | 33 (3.728) |
| 1,500 (6,672) | 55 (6.214) | | Journal Shear |
| 1,750 (7,784) | 55 (6.214) | | |
| 2,000 (8,896) | 55 (6.214) | | |
| 2,250 (10,008) | 60 (6.779) | | |
| 2,500 (11,120) | 65 (7.345) | | |
| 2,750 (12,232) | 70 (7.909) | | |
| 3,000 (13,344) | 75 (8.474) | | |
| 3,250 (14,456) | 80 (9.038) | (Stopped for inspection) | |

EXAMPLE 21

The boron-containing, heterocyclic compound, 1-hydroxy-3,7-diphenyl-5-coco-5-aza-1-bora-2,8-dioxacyclooctane, is prepared by adding 14,889 grams of cocoamine(1) and 17,516 grams of styrene oxide to a 65 liter round bottomed flask that contains 13 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product to an end point at a temperature of 400° F. (204° C.). The reaction produces 34,373 grams of 1-hydroxy-3,7-diphenyl-5-coco-5-aza-1-bora-2,8-dioxacyclooctane.

(1) Cocoamine is a mixture of primary amines consisting of approximately 52 percent dodecylamine, 19 percent of tetradecylamine, 9 percent of hexadecyl amine, 6.5 percent of octylamine, 6 percent of decylamine, 2 percent of octadecyl amine and 5 percent of a mixture of octadecenylamine and octadecadienylamine. Cocoamine is produced commercially by the Armak Company under the tradename of Armeen CD.

EXAMPLE 22

A boron-containing, heterocyclic compound is prepared by adding 17,605 grams of tallowamine(2) and 15,362 grams of styrene oxide to a 65-liter round-bottomed flask that contains 11.34 liters of oluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product to an end point temperature of 400° F. (204° C.). The reaction produces 34,695 grams of 1-hydroxy-3,7-diphenyl-5-tallow-5-aza-1-bora-2,8-dioxacyclooctane.

(2) Tallowamine is a mixture of amines consisting of approximately 29 percent hexadecylamine, 20.5 percent octadecylamine, 44 percent of a mixture of octadecenylamine and octadecadienylamine, 3 percent tetradecylamine, 1.5 percent hexadecenylamine, 1 percent heptadecylamine and 0.5 percent tetradecenylamine. Tallowamine is produced commercially by the Armak Company under the tradename Armeen T.

EXAMPLE 23

1-hydroxy-3,7-diphenyl-5-dodecyl-5-aza-1-bora-2,8-dioxacyclooctane is prepared by adding 13,502 grams of dodecylamine and 17,516 grams of styrene oxide to a 65-liter round-bottomed flask that contains 13.34 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product to an end-point temperature of 400° F. The reaction produces 321,986 grams of 1-hydroxy-3,7-diphenyl-5-dodecyl-5-aza-1-bora-2,8-dioxacyclooctane.

EXAMPLE 24

The compound, 1-hydroxy-3,6-dicresyl-5-dodecyl-5-aza-1-bora-2,8-dioxacyclooctane, is prepared by adding 21 grams of boric acid with 61.7 grams of dodecylamine, 89.3 grams of para methylstyrene oxide and 250 ml of toluene to a single-necked, one-liter, round-bottomed flask. The toluene acts as a solvent and as an azeotrope for water produced during the reaction. It should be noted that boric acid is not soluble in toluene. The flask is placed in a heating mantle and fitted with a Dean-Stark trap that is topped with a water-cooled condenser. The mixture thus formed is heated until it begins to reflux. Next, the mantle heat is adjusted to give a moderate reflux rate. The reaction mixture is refluxed for one hour, or until the stoichiometric amount of water (12ml) collects in the Dean-Stark trap and all of the boric acid has dissolved, after which the toluene is distilled from the reaction product. The reaction produces 160 grams of product.

EXAMPLE 25

The compound, 1-hydroxy-3,7-dimethyl-3,7-diphenyl-5-dodecyl-5-aza-1-bora-2,8-dioxacylooctane, is prepared by following the procedure of Example 23 with the following substitution:

Alpha methyl styrene oxide is substituted for the styrene oxide with substantially the same results.

EXAMPLE 26

Boric acid (21 grams), para-tertiary-butyl styrene oxide (119.3 grams), dodecylamine (61.7 grams) and 250 ml of toluene are mixed in a one-liter, single-necked flask to prepare 1-hydroxy-3,7-para-tertiary-butylphenyl-5-dodecyl-5-aza-1-bora-2,8-dioxacyclooctane. The flask is equipped with a heating mantle, Dean-Stark trap and water-cooled condenser. The mixture is heated under reflux until the reaction is completed; 12 ml of water collects in the Dean-Stark trap. Next, toluene is distilled from the reaction mixture. The product thus prepared is suitable for use as an extreme pressure, anti-wear and friction-reducing additive for lubricating compositions.

It should be noted that the other primary amines herein may be substituted for the dodecylamine above, to form the corresponding boron heterocyclic compound.

EXAMPLE 27

A copper derivative of 1-hydroxy-3,7-diphenyl-5-coco-5-aza-1-bora-2,8-dioxacyclooctane is prepared by following the procedure Example 21 with the following exception: the above-described compound (47 grams), 100 ml of toluene, 20 ml of triethyl amine and 10 grams of cupric acetate are mixed in a single-necked, 500 ml round-bottomed flask, equipped with a heating mantle and water-cooled condenser. The mixture is refluxed for 16 hours, then filtered and the toluene, amine, water and acetic acid (produced in situ) are distilled from the reaction product. Using the above-procedure, copper di-[1-oxy-3,7-diphenyl-5-coco-5-aza-1-bora-2,8-dioxacyclooctane] is produced.

EXAMPLE 28

A nickel derivative of 1-hydroxy-3,7-diphenyl-5-coco-5-aza-1-bora-2,8-dioxacyclooctane is prepared by following the procedure of Example 27 with the following exception:

An equivalent amount of nickel acetate is substituted for the cupric acetate. The reaction produces nickel di-[1-oxy-3,7-diphenyl-5-coco-5-aza-1-bora-2,8-dioxacyclooctane].

EXAMPLE 29

Lead di-[1-oxy-3,7-diphenyl-5-coco-5-aza-1-bora-2,8-dioxacyclooctane] is prepared in accordance with the procedure of Example 21 with the following exception:

The reaction product produced in Example 21 (23.5 grams), 100 ml of toluene, 9.5 grams of lead acetate and 10 ml of triethylamine are mixed in a single-necked 500 ml round bottomed flask, equipped with a water-cooled condenser and heating mantle. The mantle heat is adjusted until a moderate rate of reflux is obtained. The mixture thus formed is refluxed for 18 hours. Next, the mixture is filtered, and toluene, water, triethylamine and acetic acid (produced in the reaction) are distilled from the reaction product. The reaction produces lead di-[1-oxy-3,7-diphenyl-5-coco-5-aza-1-bora-2,8-dioxacyclooctane.

EXAMPLE 30

Iron di-(1-oxy-3,7-diphenyl-5-coco-5-aza-1-bora-2,8-dioxacyclooctane) is prepared according to the procedure of Example 21 with the following exception:

A mixture comprising 23.5 grams of the reaction product produced in Example 21, 100 ml of toluene, 4.3 grams of ferrous acetate and 10 ml of triethylamine are introduced into a single-necked, 500-ml, round-bottomed flask, equipped with a water-cooled condenser and heating mantle and Dean-Stark trap.

EXAMPLE 31

A boron compound of the invention is prepared by adding 17,093 grams of octadecylamine and 15,362 grams of styrene oxide to a 65-liter, round-bottomed flask that contains 13 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product to an end-point temperature of 400° F. The reaction produces 34,183 grams of 1-hydroxy-3,7-diphenyl-5-octadecyl-5-aza-1-bora-2,8-dioxacyclooctane.

EXAMPLE 32

The procedure of Example 31 is followed to produce 1-hydroxy-3,7-diphenyl-5-phenyl-5-aza-1-bora-2,8-dioxacyclooctane with the following exception:

An equivalent amount of phenylamine is substituted for octadecylamine.

EXAMPLE 33

Zinc di-[1-oxy-3,7-diphenyl-5-coco-5-aza-1-bora-2,8-dioxacyclooctane] is produced according to the procedure of Example 27 except that an equivalent amount of zinc acetate is substituted for the cupric acetate.

EXAMPLE 34

Tin di-[1-oxy-3,7-diphenyl-5-coco-5-aza-1-bora2,8-dioxacyclooctane] is prepared by substituting an equivalent amount of tin acetate for the cupric acetate in Example 27.

EXAMPLE 35

Lead di-[1-oxy-3,7-diphenyl-5-dodecyl-5-aza-1-bora-2,8-dioxacyclooctane] is prepared in accordance with the procedure of Example 23 with the following exception:

The reaction product produced in Example 23 (23.95 grams), 100 ml of toluene, 9.5 grams of lead acetate, and 10 ml of triethylamine are mixed in a single-necked, 500-ml, round-bottom flask, equipped with a water-cooled condenser, heating mantle and Dean-Stark trap. The mantle heat is adjusted until a moderate rate of reflux is obtained. The mixture thus formed is refluxed for 18 hours. Next, the mixture is filtered and the toluene, triethylamine, water and acetic acid (produced in-situ) are distilled from the reaction product. The reaction produces lead di-[1-oxy-3,7-diphenyl-5-dodecyl5-aza-1-bora-2,8-dioxacyclooctane].

EXAMPLE 36

A nickel derivative of 1-hydroxy-3,7-dicresyl-5-dodecyl-5-aza-1-bora-2,8-dioxacyclooctane is prepared by following the procedure of Example 35 with the following exception:

An equivalent amount of paramethyl styrene oxide is substituted for styrene oxide and nickel acetate is substituted for lead acetate. The reaction produces nickel di[-1-oxy-3,7-dicresyl-5-dodecyl-5-aza-1-bora-2,8dioxacyclooctane].

EXAMPLE 37

Iron di-[1-oxy-3,7-di-para-tertiary-butyl-phenyl-5-dodecyl-5-aza-1-bora-2,8-dioxacyclooctane] is prepared according to the procedure of Example 26 with the following exception:

A mixture comprising 28.4 grams of the reaction product produced in Example 26, 100 ml of toluene, 4.3 grams. of ferrous acetate and 10 ml of triethylamine are introduced into a single-necked, 500-ml, round-bottom flask, equipped with a Dean-Stark trap, water-cooled condenser and heating mantle. The heating mantle is adjusted to give a moderate rate of reflux of the reaction mixture. The mixture is refluxed for 18 hours, filtered, and the toluene, triethylamine, water and acetic acid (produced in-situ) are distilled from the reaction product.

EXAMPLE 38

Zinc di-[1-oxy-3,7-diphenyl-5-dodecyl-5-aza-1-bora-2,8-dioxacyclooctane] is produced according to the procedure of Example 35 except that zinc acetate is substituted for lead acetate.

Example 39

Tin di-[1-oxy-3,7-diphenyl-5-dodecyl-5-aza-1-bora-2,8-dioxacyclooctane] is prepared by substituting tin acetate for lead acetate in Example 35.

EXAMPLES 40 to 46

Extreme pressure, anti-wear and friction-reducing additives produced according to the procedure of Examples 21, 27, 29, 30, 33 and 34 are mixed with separate portions of 450 neutral oil at concentrations of 2 weight percent.

Each lubricant composition is tested in accordance with the procedure disclosed in ASTM:D3233-73 (Reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. A summary of the results obtained is disclosed in the following Table 9:

TABLE 9

TORQUE ON JOURNAL LB.-IN. (NEWTON-METERS)

| | | Example | | | | | |
|---|---|---|---|---|---|---|---|
| True Load lbs. (Newtons) | 40 (450 Neutral Oil) | 41 Oil with Additive of Ex. 21 | 42 Oil with Additive of Ex. 27 | 43 Oil with Additive of Ex. 29 | 44 Oil with Additive of Ex. 30 | 45 Oil with Additive of Ex. 33 | 46 Oil with Additive of Ex. 34 |
| 300 (1,334) | 9 (1.017) | 7 (0.791) | 11 (1.243) | 9 (1.017) | 10 (1.130) | 9 (1.017) | 7 (0.791) |
| 500 (2,224) | 12 (1.356) | 9 (1.017) | 15 (1.695) | 15 (1.695) | 15 (1.695) | 14 (1.582) | 9 (1.017) |
| 750 (3,336) | Journal Shear | 17 (1.921) | 21 (2.373) | 21 (2.373) | 22 (2.486) | 22 (2.486) | 16 (1.808) |
| 990 (4,404) | — | — | — | — | — | Journal Shear | — |
| 1,000 (4,448) | — | 24 (2.712) | 28 (3.163) | 30 (3.389) | 28 (3.163) | — | 19 (2.147) |
| 1,050 (4,670) | — | — | Journal Shear | Journal Shear | Journal Shear | — | 23 (2.599) |

TABLE 9-continued

| | TORQUE ON JOURNAL LB.-IN. (NEWTON-METERS) | | | | | | |
|---|---|---|---|---|---|---|---|
| | | Example | | | | | |
| True Load lbs. (Newtons) | 40 (450 Neutral Oil) | 41 Oil with Additive of Ex. 21 | 42 Oil with Additive of Ex. 27 | 43 Oil with Additive of Ex. 29 | 44 Oil with Additive of Ex. 30 | 45 Oil with Additive of Ex. 33 | 46 Oil with Additive of Ex. 34 |
| 1,250 (5,560) | — | Journal Shear | — | — | — | — | 26 (2.937) |
| 1,500 (6,672) | — | — | — | — | — | — | Journal Shear |
| 1,750 (7,784) | | | | | | | |

The above data indicate that the boron-containing, heterocyclic compounds described above impart extreme pressure properties to 450 neutral oil at concentrations of 2 weight percent.

EXAMPLES 47 and 48

The extreme pressure, anti-wear and friction-reducing additive produced in accordance with the procedure of Example 21 is mixed at a concentration of 2 weight percent with SAE 30 motor oil which contains 0.05 weight percent phosphorus. A sample of the SAE 30 motor oil which does not contain the additive of Example 21 is used as a control. This control was blended 6.5 volume percent (7.05 weight percent) Amoco PCO-059 in Union 450 neutral. (See footnote (E) in Table 12 hereafter.)

Each lubricant composition is tested in accordance with the procedure disclosed in ASTM D3233-73 (Reapproved 1978) using a Falex lubricant tester. A summary of the results in disclosed in the following Table 10:

TABLE 10

| | Torque on Journal lbs.-in (Newton-Meters) | |
|---|---|---|
| Example | 47 | 48 |
| True Load lbs. (Newtons) | Control (SAE 30 Motor Oil) | SAE 30 Motor Oil with Additive of Ex.21 |
| 300 (1,334) | 9 (1.017) | 8 (0.904) |
| 500 (2,224) | 14 (1.582) | 12 (1.356) |
| 750 (3,336) | 20 (2.260) | 17 (1.921) |
| 950 (4,404) | Journal Shear | — |
| 1,000 (4,448) | — | 22 (2.486) |
| 1,250 (5,560) | — | 28 (3.163) |
| 1,400 (6,227) | — | Journal Shear |

The extreme pressure property of SAE 30 motor oil is substantially enhanced in Table 10 above when 2 weight percent of 1-hydroxy-3,7-diphenyl-5-coco-5-aza-1-bora-2,8-dioxacyclooctane is added to said SAE 30 motor oil.

EXAMPLE 49

A copper corrosion inhibitor comprising 1,3,4-thiadiazole-2,5-bis(dodecyldisulfide) is prepared by chlorinating 284 grams of n-dodecyl mercaptan in 0.6 liter of carbon tetrachloride with 1.47 moles of chlorine over a two-hour period at a temperature of about 23° F. (−5° C.) to about 32° F. (0° C.). Next, sulfenyl chloride which forms as a reaction product is stripped with nitrogen to remove hydrogen chloride, and the resultant compound is added to 86 grams of a 2,5-dimercapto-1,3,4-thiadiazole slurry. The mixture is heated at 86° F. (30° C.) for 1 and ½ hours and the resultant compound (1,3,4-thia-diazole-2,5-bis(dodecyldisulfide) is recovered by washing with water and sodium bicarbonate and vacuum stripping to remove carbon tetrachloride.

EXAMPLE 50

The procedure of Example 49 is followed to prepare 1,3,4-thiadiazole-2,5-bis (octyldisulfide) with the following exception: octyl mercaptan is substituted for the dodecylmercaptan.

EXAMPLE 51

The oxidation inhibitor, thiodiethyl bis-(3,5-di-t-butyl-4-hydroxy) hydrocinnamate, is prepared by melting together 17.95 weight percent of beta,beta'-dihydroxydiethyl sulfide, 81.41 weight percent of (3,5-di-t-butyl4-hydroxy) hydrocinnamate acid and 0.64 weight percent of sodium methylate under a nitrogen atmosphere at 266° F. (130° C.) for two and one-half hours. Methanol thus formed is separated from the reaction mixture and condensed in a dry-ice trap using nitrogen gas as a carrier. The reactants are heated at 149° F. (65° C.) for three hours and the reaction product is dissolved in warm benzene, filtered and the benzene filtrate is washed three times with saturated sodium chloride solution. The filtrate is, next, dried over anhydrous sodium sulfate and the solvent evaporated using conventional techniques. Thiodiethyl bis-(3,5-di-t-butyl-4-hydroxy) hydrocinnamate is isolated and purified by successive recrystallization from hexane and a mixture of hexane and t-butanol.

EXAMPLE 52

The oxidation inhibitor, bis(dithiobenzil) iron (II), is prepared by adding 400 grams of benzoin and 600 grams of phosphorous sulfide to a single-necked, 5-liter, round-bottomed flask equipped with heating mantle and water-cooled condenser and containing 1,500 ml of dioxane. The mixture thus formed is refluxed for two hours. Next, 200 grams of hydrated ferrous chloride dissolved in 500 ml of water is added to the 5 liter flask and the mixture is heated on a steam bath at 212° F. (100° C.) for 2 hours. The reaction product thus formed (169.5 grams) is filtered and washed with methanol.

EXAMPLE 53

Dodecylamino di(phenylethylate) hydrogen borate is prepared by adding 34.85 pounds (15,808 grams) of dodecylamine (1 equivalent) and 41.0 pounds (18,597 grams) of styrene oxide (2 equivalents) to A 17 U.S. gallon (64.3 liters) round bottomed flask equipped with a water-cooled condenser and containing 3 U.S. gallons (11.36 liters) toluene and 1 liter of water. The reaction is exothermic and begins immediately upon addition of the above reactants. Additional heat is applied and the reaction mixture is refluxed for a total of 24 hours; however, as little as 2 hours may result in complete reaction.

The reaction is cooled to room temperature, 10.49 pounds (4,758.16 grams) of boric acid (1 equivalent) is added and the flask is equipped with a Dean-Stark trap. Heat is again applied and the reaction mixture refluxed until water stops collecting in the trap. Toluene is, then, distilled from the reaction product at a temperature of 400° F. (204° C.) or less. About 6 liters of water collect in the Dean-Stark trap. The reaction produces approximately 75 pounds (34,019 grams) of product.

EXAMPLE 54 to 60

A lubricant composition containing dodecylamino di(phenylethylate) hydrogen borate, 1,3,-4-thiodiazole-2,5-bis(octyldisulfide), terephthalic acid, and thiodiethyl bis-(3,5-di-t-butyl-4-hydroxy) hydrocinnamate is tested for copper and lead corrosion inhibition and anti-oxidant properties using a single-cylinder Labeco CLR Test Engine equipped with sintered copper (65 wt. %)/lead (35 wt. %) connecting rod bearings, in accordance with the procedure of Federal Test Method Standard No. 791B, method 3405.2. The same lubricant composition, but containing bis(dithiobenzil)iron(II) substituted for the hydrocinnamate compound, is also tested by the same procedure.

The copper-lead corrosion tests are conducted in accordance with the test conditions of the following Table 11:

TABLE 11

| Operating Conditions | |
|---|---|
| Test Duration, Hours | 40 |
| Speed, RPM | 3150 ± 25 |
| Load, BHP | 6.5a |
| (KW) | (4.85) |
| Fuel, Flow, Lb/Hr. | 4.75 ± 0.25 |
| (gm/Hr.) | (2,155 ± 5) |
| Air/Fuel Ratio | 14.0 ± 0.5 |
| Jacket Outlet Coolant Temp.,°F. | 200 ± 2 |
| (°C.) | (93.33 ± 1.11) |
| Gallery Oil Temp., °F. | 290 ± 2 |
| (°C.) | (143.33 ± 1.11) |
| Spark Advance, BTDC | 35 ± 1 |
| Oil Pressure, PSIG | 40 ± 2 |
| (atmospheres) | (3.72) |
| Crankcase Vacuum, in. $H_2O$ | 2 ± 0.5 |
| (cm. $H_2O$) | (5.08 ± 1.27) |
| Exhaust Back Pressure, in. Hg. | 0.5 ± 0.5 |
| (cm. Hg) | (1.27 ± 1.27) |
| Crankcase Off-Gas, CFH | 30 ± 1 |
| (CMH) | (0.83 ± .03) |
| Oil Charge, Pints | 3.5 |
| (Liters) | (1.66) |

The test is conducted by charging 3.5 pints (1.66 liters) of the test lubricant to the engine sump. Test duration consists of 40 hours operation at the prescribed test conditions of Table 11 above. When the prescribed gallery oil temperature is reached, the test time begins. Interim oil adjustments are made at the end of 10, 20 and 30 hours of test operation. A copper/lead bearing weight loss (BWL) of about 40 mg of lower is considered acceptable. All of the tests are conducted on blends based upon the control using SAE 30 motor oil further containing the additives and/or compounds, at the concentrations in the following Table 12:

TABLE 12

| Example | Heterocyclic Compound of Ex. 53 (A) (Wt. %) | Copper Corrosion Inhibitor (B) (Wt. %) | Terephthalic Acid (Wt. %) | Anti-Oxidant (Wt. %) | Phosphorous (Wt. %) | Amoco (E) PCO-059 (Vol. %) | CRC L-38 Engine Test 40 hours (BWL, mg) (F) |
|---|---|---|---|---|---|---|---|
| Control 47 | — | — | — | — | 0.05 | 6.5 | 24.0 |
| 54 | 2.12 | — | — | — | 0.05 | 6.5 | 93 |
| 55 | 2.12 | 0.050 | 0.01 | — | 0.05 | 6.5 | 43.0 |
| 56 | 2.12 | 0.075 | 0.01 | — | 0.05 | 6.5 | 40.0 |
| 57 | 2.12 | 0.075 | 0.01 | — | 0.05 | 6.5 | 33.4 |
| 58 | 2.00 | 0.03 | 0.006 | — | 0.05 | 6.5 | 38 |
| 59 | 2.12 | 0.075 | 0.01 | 0.05(C) | 0.05 | 6.5 | 26.4 |
| 60 | 2.00 | 0.075 | 0.01 | 0.05(D) | 0.05 | 6.5 | 34.8 |

(A) Dodecylamino di(phenylethylate) hydrogen borate.
(B) Copper Corrosion Inhibitor = A mixture of 83 weight percent 1,3,4-thiodiazole-2,5-bis(octyl-disulfide) and 17 weight percent of 2 mercapto-5 octyldithio-1,3,4-thiadiazole, marketed under the Tradename of Amoco 150 by the Amoco Oil Company.
(C)Thiodiethyl bis-(3,5-di-t-butyl-4-hydroxy) hydrocinnamate.
(D)Bis(dithiobenzil)iron(II).
(E) Amoco PCO-059 = detergent/dispersant package marketed commercially by the Amoco Oil Company.
(F) BWL = bearing weight loss.

EXAMPLE 61

The bis(hydrocarbyloxy methylated) boron-containing heterocyclic compound, 1-hydroxy-3,7-di(methyl phenoxy methyl)-5-coco-5-aza-1-bora-2,8-dioxacyclooctane, is prepared by adding 278.5 grams of cocoamine and 450.5 grams of cresyl glycidyl ether to a 2-liter round-bottomed flask that contains 250 ml of toluene and 22 ml of water. The flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 86.0 grams o boric acid are added to the flask. Then, the flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 86.0 grams of boric acid are added to the flask. Then the flask is equipped with a Dean-Stark trap topped with a water-cooled condenser and the reaction mixture is refluxed until water stops collecting in the trap. Toluene is distilled from the reaction product to an end-point temperature of 400° F. (204° C.). The reaction produces 758.5 grams of 1-hydroxy-3,7-di(methyl-phenoxymethyl)-5-coco-5-aza-1-bora-2,8-dioxacyclooctane.

EXAMPLE 62

The bis(hydroxycarbyloxymethylated) boron-containing, heterocyclic compound, 1-hydroxy-3,7-di(-methyl-phenoxymethyl)-5-oleyl-5-aza-1-bora-2,8-dioxacyclooctane, is prepared by adding 55.6 grams of oleyl amine and 66.0 grams of cresyl glycidyl ether to a 1-liter round-bottomed flask that contains 250 ml of toluene.

The flask is placed in a heating mantle and fitted with a water-cooled condenser. The mixture thus formed is heated until it begins to reflux. Next, the temperature is adjusted to give a moderate reflux rate and the reaction mixture is refluxed for 18 hours. The reaction mixture is cooled to room temperature and 12.4 grams of boric acid are added to the flask. Then, the flask is equipped with a Dean-Stark trap topped with a water-cooled condenser and the reaction mixture is refluxed until water stops collecting in the trap. Toluene is distilled from the reaction product to an end point temperature of 400° F. (204° C.). The reaction produces 97 grams of 1-hydroxy-3,7-di-(methyl-phenoxymethyl)-5-oleyl-5-aza-1-bora-2,8-dioxacyclooctane.

EXAMPLE 63

The compound, 1-hydroxy-3,7-di(methyl phenoxy methyl)-5-dodecyl-5-aza-1-bora-2,8-dioxacyclooctane, is prepared in accordance with the procedure of Example 61 with the following exception: one mole of dodecylamine is substituted for each mole of cocoamine used.

EXAMPLE 64

The compound, 1-hydroxy-3,7-di(methyl phenoxy methyl)-5-tallow-5-aza-1-bora-2,8-dioxacyclooctane, is prepared in accordance with the procedure of Example 62 with the following exception: one mole of tallowamine is substituted for each mole of oleyl amine used.

EXAMPLE 65

A copper derivative of 1-hydroxy-3,7-di(methyl phenoxy methyl)-5-coco-5-aza-1-bora-2,8-dioxacyclooctane is prepared by following the procedure of Example 61 with the following exception: the compound of Example 61 (47 grams), 100 ml of toluene, 20 ml of triethyl amine and 10 grams of cupric acetate are mixed in a single-necked, 500 ml round bottom flask, equipped with a heating mantle, Dean-Stark trap and water-cooled condenser. The mixture is refluxed for 16 hours, then filtered and the toluene, amine, water and acetic acid (produced in situ) are distilled from the reaction product. Using the above procedure, copper di[1-oxy-3,7-di(methyl phenoxy methyl)-5-coco-5-aza-1-bora-2,8-dioxacyclooctane] is produced.

EXAMPLE 66 to 71

The compound 1-hydroxy-3,7-di-(methylphenoxymethyl)-5-coco-5-aza-1-bora-2,8-dioxacyclooctane produced in accordance with the procedure of Example 61 is tested for extreme pressure, anti-wear and friction-reducing properties admixed with separate portions of 450 neutral oil and SAE 30 motor oil at concentrations of 1 and 2 weight percent respectively. Samples of 450 neutral oil and the control SAE 30 motor oil (Example 47) without the compound 1-hydroxy-3,7-di-(methyl-phenoxymethyl)-5-coco-5-aza-1-bora-2,8-dioxacyclooctane serve as controls of the experiments.

Each lubricant composition is tested in accordance with the procedure disclosed in ASTM:D3233-73 (Reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks(-steel) are submerged in the lubricant composition to be tested. A summary of the results obtained is disclosed in the following Table 13:

TABLE 13

TORQUE ON JOURNAL LB.-IN. (NEWTON-METERS)

| True Load Lbs. (Newtons) | Example 66 450 Neutral Oil | Example 67 450 Neutral Oil with 1 wt. % Additive of Ex. 61 | Example 68 450 Neutral Oil with 2 wt. % Additive of Ex. 61 | Example 69 SAE 30 Motor Oil (Ex. 47) | Example 70 SAE 30 Motor Oil with 1 wt. % Additive of Ex. 61 | Example 71 SAE 30 Motor Oil with 2 wt. % Additive of Ex. 61 |
|---|---|---|---|---|---|---|
| 300 (1,334) | 8 (0.904) | 7 (0.791) | 6 (0.678) | 12 (1.356) | 7 (0.791) | 8 (0.904) |
| 500 (2,224) | 14 (1.582) | 10 (1.130) | 10 (1.130) | 17 (1.921) | 12 (1.356) | 11 (1.243) |
| 600 (2,669) | xxx[1] | — | — | — | — | — |
| 750 (3,336) |  | 18 (2.034) | 17 (1.921) | 30 (3.389) | 16 (1.808) | 15 (1.695) |
| 800 (3,558) |  | — | — | xxx | — | — |
| 1,000 (4,448) |  | xxx | 20 (2.260) |  | 25 (2.825) | 20 (2.260) |
| 1,100 (4,893) |  |  | xxx |  | — | — |
| 1,250 (5,560) |  |  |  |  | xxx | 26 (2.937) |
| 1,500 (6,672) |  |  |  |  |  | xxx |

[1] xxx indicates failure occurred with the journal scoring and the shear pin breaking.

As shown in Table 13, the addition of 1-hydroxy-3,7-di-(methylphenoxymethyl)-5-coco-5-aza-1-bora-2,8-dioxacyclooctane to 450 neutral oil and to the control SAE 30 motor oil (Example 47) at concentrations of one and two weight percent, respectively, imparts extreme pressure properties to the oils.

EXAMPLE 72

A lubricant composition is tested for copper and lead corrosion inhibition properties using a single-cylindered Labeco CLR Test Engine equipped with sintered copper (65 wt. %)/lead (35 wt. %) connecting rod bearings, in accordance with the procedure of Federal Test Method Standard No. 791B, Method 3405.2.

The test is conducted in accordance with the test conditions of Table 11 in previous Examples 54 to 60.

In addition, the test is conducted by charging 3.5 pints (1.7 liters) of the test lubricant to the engine sump. Test duration consists of 40 hours operation at the prescribed test conditions of Table 11 above. When the prescribed gallery oil temperature is reached, the test time begins. Interim oil adjustments are made at the end of 10, 20 and 30 hours of test operation. A copper/lead bearing weight loss (BWL) of about 40 mg or lower is considered acceptable.

The lubricant composition tested in this Example 72 is a standard 450 neutral oil containing the additives and concentrations shown in Table 14. Also shown in Table 14 is the result of the experiment.

TABLE 14

| Example | Compound of Example 61 (Wt. %) (A) | Copper Corrosion Inhibitor (B) (Wt. %) | Terephthalic Acid (Wt. %) | Anti-Oxidant (C) (Wt. %) | Amoco (D) PCO-059 (Wt. %) | CRC L-38 Engine Test 40 hours (BWL, mg) (E) |
|---|---|---|---|---|---|---|
| 72 | 2.12 | 0.075 | 0.010 | 0.050 | 7.050 | 30.1 |

(A) 1-hydroxy-3,7-di-(methylphenoxymethyl)-5-coco-5-aza-1-bora-2,8-dioxacyclooctane (Example 61).
(B) Copper Corrosion Inhibitor = A mixture of 83 weight percent 1,3,4-thiodiazole-2,5-bis(octyldisulfide) and 17 weight percent of 2 mercapto-5-octyldithio-1,3,4-thiadiazole, marketed by the Amoco Oil Company under the trademark of Amoco 150.
(C) Anti-oxidant = thiodiethyl bis(3,5-di-t-butyl-4-hydroxy) hydrocinnamate.
(D) Amoco PCO-059 = detergent/dispersant package marketed commercially by the Amoco Oil Company.
(E) BWL = bearing weight loss.

EXAMPLE 73

A lubricant composition containing 450 neutral oil, 1-hydroxy-3,7-diphenyl-5-coco-5-aza-1-bora-2,8-dioxacyclooctane, and octyl diphenyl amine is tested for extreme pressure properties, and resistance to oxidation stability, and corrosion using a single-cylinder Labeco CLR Test Engine equipped with sintered copper (65 wt. %)/ lead (35 wt. %) connecting rod bearings, in accordance with the procedure ASTM STP 509A, Part IV and the engine operating conditions of Examples 54 to 60 and 72. The total phosphorus content was 0.075 weight percent.

The results are summarized in the following Table 15:

TABLE 15

| Example | E.P. Additive (A) (wt. %) | Anti-oxidant (B) (wt. %) | Copper Corrosion (C) Inhibitor (wt. %) | OLOA 267 (D) (wt. %) | AMOCO (E) PCO-059 (wt. %) | UNAD (F) 242 (wt. %) | CRC L-38 Engine Test 40 hours (BWL, mg) (G) |
|---|---|---|---|---|---|---|---|
| 73 | 2.67 | 0.50 | 0.15 | 0.30 | 7.05 | 0.01 | 15.4 |

(A) E.P. Additive = 1-hydroxy-3,7-diphenyl-5-coco-5-aza-1-bora-2,8-dioxacyclooctane (Example 21).
(B) Anti-oxidant = 4 octyldiphenyl amine.
(C) Copper Corrosion Inhibitor = a mixture of 83 weight percent 1,3,4-thiodiazole -2,5-bis (octyldisulfide) and 17 weight percent of 2-mercapto-5-octyldithio-1,3,4-thiodiazole.
(D) OLOA 267 = zinc dialkyl dithiaphosphate marketed commercially by the Chevron Chemical Company.
(E) AMOCO PCO-059 = detergent/dispersant package marketed commercially by the Amoco Oil Company.
(F) UNAD 242 = Silicone-type defoamant containing kerosene.
(G) BWL = bearing weight loss, e.g. a BWL of 40 mg or less is acceptable.

EXAMPLE 74

The lubricant composition disclosed in Table 15 of Example 73 is tested in a 1977 Oldsmobile V-8 engine for 64 hours in accordance with the following 1977 General Motors Lubricant Evaluation Sequence III D test.

Prior to each test run, the engine is completely disassembled, solvent cleaned, measured and rebuilt in strict accordance to furnished specifications. Following the preparation, the engine is installed on a dynamometer test stand equipped with the appropriate accessories for controlling speed, load, temperatures and other various engine operating conditions.

The engine is operated on a 4-hour break-in-schedule after which oil is sampled and leveled. The engine is then operated under non-cyclic, moderately high speed, high load and temperature conditions for a test duration of 64 hours, with oil leveling and oil additions each 8 hours.

In the following Table 16 is a summary of these operating conditions:

TABLE 16

| | |
|---|---|
| Speed, rpm | 3000 ± 20 |
| Load, bhp | 100 ± 2 |
| (Kw) | (74.6 ± 1.49) |
| Oil, to engine, after filter, °F. | 300 ± 2 |
| (°C.) | (149 ± 1.1) |
| Oil pump outlet, psig min | 40 |
| (atmospheres min) | (3.72) |
| Coolant, jacket out, °F. | 245 ± 1 |
| (°C.) | (18.3 ± 0.6) |
| jacket in, °F. | 235 ± 1 |
| (°C.) | (112.8 ± 0.6) |
| jacket flow rate, gpm | 60 ± 1 |
| (lpm) | (227 ± 3.8) |
| rocket cover out, °F. | 240 ± 3 |
| (°C.) | (115.56 ± 1.67) |
| at gpm per cover | at 1.5 ± 0.5 |
| (lpm) | (5.7 ± 1.9) |
| breather tube out, °F. | 100 ± 2 |
| (°C.) | (37.8 ± 1.1) |
| at gpm | at 3.0 ± 0.5 |
| (lpm) | (11.36 ± 1.9) |
| Air-fuel ratio | 16.5 ± 0.5 |
| Carburetor, air temperature, °F. | 80 ± 2 |
| (°C.) | (26.7 ± 1.1) |
| Carburetor, air humidity, grains per lb of dry air | 80 ± 5 |
| (grams per gram of dry air) | (0.01143 ± 0.0007) |
| Carburetor, pressure, in. of water | 0.1 to 0.3 |
| (cm) | (.3 to .8) |
| Blowby rate, cfm at 100° F. and 29.7 in. | 2.0 ± 0.3 |
| (37.78° C.) and (75.4 cm) of Hg | (0.0566 ± 0.0085) |
| Intake manifold vacuum, in. of Hg | 7 ± 2 |
| (cm) | (17.78 ± 5.08) |
| Exhaust back pressure, in. of water | 30 ± 2 |
| (cm) | (76.2 ± 5.08) |
| Exhaust back pressure, max differential, in. (cm) of water | 0.2 (0.51) |

After every 8 hours of testing, a 25-minute shutdown period is provided for oil sampling, additions and level adjustments. The total running test time for Sequence IIID is 64 hours. The results are summarized in the following Table 17:

TABLE 17

| Test | Result | API "SF" Limit |
|---|---|---|
| (A) Engine Sludge Rating (10 = clean) | 9.5 | 9.2 min. |
| (B) Piston Varnish (10 = clean) | 9.4 | 9.2 min. |
| (C) Cam & Lifter Wear (inch) | 0.0019 | 0.0080 max. |
| (D) 64 hour Viscosity increase, % | 182 | 375 max. |
| (E) Oil Consumption, quarts | 3.06 | 6.38 max. |

The engine tests are performed in accordance with the Coordinating Research Council (CRC) rating and techniques located in CRC Manual NOS 9 and 12.

EXAMPLE 75

A sulfurized, boron-containing, heterocyclic compound is prepared by mixing 12 grams of oleylamine, 9.6 grams of styrene oxide and 200 ml of toluene for 30 minutes at room temperature (25° C.) in a single-necked one-liter round-bottomed flask. The flask is placed in a heating mantle and equipped with a water-cooled condenser. The mixture is heated under reflux for three hours producing an oleylamine/styrene oxide adduct.

The adduct is cooled to room temperature and 2.47 grams of boric acid is added to the flask. Next, the resulting mixture is refluxed until 1.44 ml of water collects in an added Dean-Stark trap. The flask and contents are moved to a rotary evaporator where toluene is stripped from the boron-containing, heterocyclic compound (18 grams).

Sulfur (0.96 grams) and 75 ml of toluene are added to the round-bottomed flask and the resulting mixture is heated to reflux temperature with mixing for four hours, after which the toluene is distilled off under vacuum, to yield the desired reaction product.

EXAMPLE 76

The reaction product of Example 75 is tested for extreme pressure properties in 450 neutral oil in accordance with the procedure disclosed in ASTM:D 32 33-73 (Reapproved 1978) using a Falex lubricant tester. The test is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. The results are summarized in the following Table 18:

TABLE 18

| | Torque on Journal lb.-in. (Newtons-Meters) | |
|---|---|---|
| True Load lbs. (Newtons) | 450 Neutral Oil (A) without additive | 450 Neutral Oil (A) with 2.25 wt.% additive |
| 300 (1,334) | 9 (1.017) | 2 (0.226) |
| 500 (2,224) | 12 (1.356) | 4 (0.452) |
| 750 (3,336) | xx | 8 (0.904) |
| 1,000 (4,448) | | 13 (1.469) |
| 1,250 (5,560) | | 18 (2.034) |
| 1,500 (6,672) | | 23 (2.599) |
| 1,750 (7,784) | | xx |

(A) 450 Neutral Oil, marketed commercially by Union Oil Company of California.

EXAMPLE 77

A sulfochlorinated, boron-containing, heterocyclic compound is produced by adding 20 grams of 1-hydroxy3,7-diphenyl-5-oleyl-5-aza-1-bora-2,8-dioxacyclooctane, 10 ml of toluene and 1.76 grams of sulfur monochloride to a one liter round-bottomed flask equipped with heating mantle and water- cooled condenser. The mixture thus formed is heated at 200° F. (93.33° C.) for 45 minutes, then 6.3 grams of 450 neutral oil is added to the flask and the toluene evaporated. The compound 10,10′-dithiodi[9-chloro-1-(5-hydroxy-3,7-diphenyl-1-aza-4,6-diocta-5-bora-cyclooctyl)-octadecane] is produced in this reaction.

EXAMPLE 78

The compound dithiodi-[1-(5-hydroxy-3,7-diphenyl-aza-4,6-diocta-5-bora-cyclooctyl)-chlorotallow] is produced in accordance with the procedure of Example 75 with the following exception:

20 grams of 1-hydroxy-3,7-diphenyl-5-tallow-5-aza-1-bora-2,8-dioxacyclooctane and 1.215 grams of sulfur monochloride are added to the one liter round-bottomed flask.

EXAMPLE 79 to 81

The compounds produced in Examples 77 and 78 are tested for extreme pressure properties by admixing each compound with separate portions of 450 neutral oil at concentrations of 2 weight percent. A sample of 450 neutral oil without an additive (compound) serves as a control in the experiment.

Each lubricant composition is tested in accordance with the procedure disclosed in ASTM:D 32 33-73 (Reapproved 1978) using a Falex lubricant tester containing a steel journal and V-blocks. A summary of the results obtained disclosed in the following Table 19:

TABLE 19

| TORQUE ON JOURNAL LB.-IN. (NEWTON-METERS) | | | |
|---|---|---|---|
| Example | 79 | 80 | 81 |
| True Load Lbs. (Newtons) | 450 Neutral Oil | 450 Neutral Oil with 2 wt. % Additive of Ex. 77 | 450 Neutral Oil with 2 wt. % Additive of Ex. 78 |
| 300 (1,334) | 9 (1.017) | 2 (0.226) | 4 (0.452) |
| 500 (2,224) | 14 (1.587) | 3 (0.339) | 6 (0.678) |
| 750 (3,336) | 20 (2.260) | 8 (0.904) | 10 (1.130) |
| 1,000 (4,448) | xxx[(1)] | 9 (1.017) | 14 (1.582) |
| 1,250 (5,560) | | 11 (1.243) | 18 (2.034) |
| 1,500 (6,672) | | 13 (1.469) | 21 (2.373) |
| 1,750 (7,784) | | 13 (1.469). | 23 (2.599) |
| 2,000 (8,896) | | xxx | 24 (2.712) |
| 2,250 (10,008) | | | xxx |

[(1)]xxx indicates failure occurred with the journal scoring and the shear pin breaking.

EXAMPLE 82

A chlorinated, boron-containing, heterocyclic compound is prepared by placing 71.3 grams of a mixture containing 75 weight percent of 1-hydroxy-3,7-diphenyl-5-tallow-5-aza-1-bora-2,8-dioxacyclooctane and 25 weight percent of 450 neutral oil into a 250 ml Pyrex flask equipped with a side arm. Chlorine gas is introduced into the flask through a Tygon tube attached to a glass tube equipped with a rubber stopper and extending to the bottom of the flask. The chlorine gas is bubbled through the heterocyclic compound with agitation. Excess gas is vented through the side arm of the flask, Tygon tubing and glass tubing into an aqueous solution of 10% potassium hydroxide. The chlorine gas was bubbled through the system for 15 minutes giving a total weight gain of 3.2 grams to the heterocyclic compound. The compound thus produced is 1-hydroxy-3,7-diphenyl-5-(perchlorotallow)-1-bora-2,8-dioxa-5-aza-cyclooctane.

EXAMPLE 83

A brominated, boron-containing, heterocyclic compound is prepared by placing 71.33 grams of a mixture containing 75 weight percent of 1-hydroxy-3,7-diphenyl-5-tallow-5-aza-1-bora-2,8-dioxacyclooctane and 25 weight percent of 450 neutral oil into a 250 ml Pyrex flask equipped with a heating mantle and thermometer.

Liquid bromine (6.37 grams) is added to the Pyrex flask and the mixture is agitated for ten minutes. Next the mixture is heated at 120° F. (49° C.) for ten minutes. The compound 1-hydroxy-3,7-diphenyl-5-(perbromotallow)-1-bora-2,8-dioxa-5-aza-cyclooctane is produced.

EXAMPLE 84 to 88

The compounds produced in Examples 82 and 83 are tested for extreme pressure properties by admixing each compound with separate portions of SAE 30 motor oil containing 0.05 weight percent phosphorus (added as zinc dialkyl dithiophosphate) and the concentration of additive indicated in Table 20 below. A sample of the control SAE 30 motor oil (Example 47) without an additive (borate of the present invention) serves as a control in the experiment.

Each lubricant composition is tested in accordance with the procedure disclosed in ASTM:D 32 33-73 (Reapproved 1978) using a Falex lubricant tester containing a steel journal and V-blocks. A summary of results obtained is disclosed in the following Table 20:

Into a test tube was placed sufficient water and lubricating oil containing the boron compound to be tested so that the water and oil each formed about 50 percent of the contents of the test tube. The contents were then shaken vigorously, after which the test tube was visually inspected to see if an emulsion had formed (indicative of water instability) or if two separate, clearly defined phases settled out (indicative of water stability).

Upon visual inspection of the various samples, it was found that the boron compound of formula (II) consistently produced a clearly defined, two-phase liquid indicative of a boron additive stable to water in a lubricating environment. In contrast, the formula (I) compound consistently formed an emulsion indicative of instability in the presence of water in a lubricating environment.

In yet other tests, it was found that the formula (II) compounds were less corrosive to lead and copper bearings in automotive engines and the like than the above-described formula (I) compounds.

From these tests, and the data shown in previous examples, the following was concluded: although the formula (I) compound is a highly useful lubricating oil

TABLE 20

| | TORQUE ON JOURNAL LB.-IN. (NEWTON-METERS) | | | | |
|---|---|---|---|---|---|
| Example | 84 | 85 | 86 | 87 | 88 |
| True | (SAE 30 Oil) | Oil with Additive | Oil with Additive | Oil with Additive | Oil with Additive |
| Load | Control | of | of | of | of |
| lbs. (Newtons) | 47 | Ex. 83 (1 wt. %) | Ex. 82 (1 wt. %) | Ex. 82 (2 wt. %) | Ex. 82 (5 wt. %) |
| 300 (1,334) | 13 (1.469) | 9 (1.017) | 9 (1.017) | 8 (0.904) | 6 (0.678) |
| 500 (2,224) | 16 (1.808) | 15 (1.695) | 13 (1.469) | 11 (1.243) | 8 (0.904) |
| 750 (3,336) | 30 (3.389) | 22 (2.486) | 20 (2.260) | 20 (2.260) | 12 (1.356) |
| 755 (3,358) | Shear | — | — | — | — |
| 950 (4,226) | — | Shear | — | — | — |
| 1,000 (4,448) | — | — | 25 (2.825) | 24 (2.712) | 16 (1.808) |
| 1,100 (4,893) | — | — | Shear | — | — |
| 1,250 (5,560) | — | — | — | 30 (3.389) | 19 (2.147) |
| 1,300 (5,782) | — | — | — | Shear | — |
| 1,450 (6,450) | — | — | — | — | Shear |

The above data indicate that the boron-containing heterocyclic compounds described above impart extreme pressure lubricating properties to SAE 30 motor oil at the indicated concentrations.

EXAMPLE 89

Tests were conducted to determine the effects on water stability of various boron-containing compounds of formula (I) hereinbefore wherein $R_1$ and R were unsubstituted ethylene groups, M was hydrogen, and R contained between 8 and 20 carbon atoms and was either an alkyl group or an alkenyl group with only one double bond in the chain. The same tests were also conducted to determine the water stability of various boron-containing compounds of formula (II) hereinbefore wherein $R_4$, $R_7$, $R_8$, $R_9$, $R_{10}$, $R_{11}$, and M were hydrogen, $R_5$ and $R_6$ were unsubstituted phenyl radicals (i.e., a benzene ring), and $R_3$ varied as R in formula (I) discussed above.

The purpose of the experiment was to determine if, in the presence of water, said boron compounds would form an emulsion. All lubricating oils contain water (or come into contact with water) to some extent, and to the degree that the boron compound resists forming an emulsion in oil-water mixtures, to that same extent is it a more desirable additive for engine lubricating oils.

The tests were conducted as follows:

additive, particularly in situations wherein the water concentration of the oil can be minimized, the formula (II) compound possessed unexpectedly superior properties thereto with respect to water stability and corrosion inhibition.

EXAMPLE 90

The boron-containing heterocyclic compounds listed in Table 21 below were tested for oil solubility by adding 2 grams of each compound and separate samples of 98 grams of 450 neutral oil to 250 ml Pyrex beakers equipped with teflon-coated, magnetic stirring bars which had lengths of 1½ inches and diameter of ¼ inch. The Pyrex beakers were placed on Model PC-351 Corning hot plates and the boron-containing heterocyclic compound-450 neutral oil mixtures were heated at temperatures of 120° F. with stirring (400 RPM of stirring bars) for ten minutes.

The Pyrex beakers were removed from the hot plates and the boron-containing heterocyclic compound-450 neutral oil mixtures were examined for oil solubility of said compound in each sample. The results are summarized in the following Table 21:

TABLE 21

Oil Solubility Chart

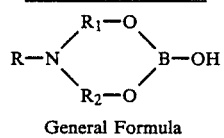

General Formula

| Compound Name | R | $R_1$ and $R_2$ | Solubility |
|---|---|---|---|
| 1. Methylamine di(ethylate)hydrogen borate | Methyl ($C_1$) | $C_2$ Carbon Chain | Insoluble |
| 2. Octylamine di(ethylate)hydrogen borate | Octyl ($C_8$) | $C_2$ Carbon Chain | Insoluble |
| 3. Octylamine di(-2-methylethylate)hydrogen borate | Octyl ($C_8$) | $C_3$ Carbon Chain | Insoluble |
| 4. Octylamine di(-2-ethylethylate)hydrogen borate | Octyl ($C_8$) | $C_4$ Carbon Chain | Insoluble |
| 5. Dodecylamine di(-2-methylethylate)hydrogen borate | Dodecyl ($C_{12}$) | $C_3$ Carbon Chain | Soluble |
| 6. Dodecylamine di(-2-ethylethylate)hydrogen borate | Dodecyl ($C_{12}$) | $C_4$ Carbon Chain | Soluble |
| 7. Cocoamine di(-2-ethylethylate)hydrogen borate | Coco ($C_{12}$ average) | $C_4$ Carbon Chain | Soluble |
| 8. Octadecyl di(-2-methylethylate)hydrogen borate | Octadecyl ($C_{18}$) | $C_3$ Carbon Chain | Soluble |
| 9. Tallow di(-2-methylethylate)hydrogen borate | Tallow ($C_{18}$ average) | $C_3$ Carbon Chain | Soluble |

The data in Table 21 show that boron-containing heterocyclic compounds are not soluble in 450 neutral oil at concentrations of 2 weight percent when the R group attached to the nitrogen atom of said compounds contains 8 or less carbon atoms. In contrast, boron-containing heterocyclic compounds are soluble in 450 neutral oil at concentrations of 2 weight percent when the R group contains 12 or more carbon atoms.

Based on these data, it is concluded that the oil solubility of the boron-containing heterocyclic compounds is directly related to the length of the carbon chain in the R group attached to the nitrogen atom of the amine moiety in said boron-containing heterocyclic compound, and that boron-containing heterocyclic compounds with 9 or more carbon atoms in the R group attached to the nitrogen atom of the amine moiety of said compounds are more soluble in oil than when said R group contains 8 or less carbon atoms:

Several other factors should also be considered when assessing the data in Table 21. One such is that the data are indicative of solubilities in a specific oil, i.e., a 450 neutral oil, and that for other oils, e.g., silicone synthetic oils, some of the boron compounds shown as insoluble may prove soluble. Thus, the data indicate the relative solubility of one boron compound versus another, not the absolute solubility of boron compounds in all oils. Another factor to be considered is the effect of the length of the $R_1$ and $R_2$ groups. The data clearly indicate, when these groups contain only about 4 carbon atoms or less, that the solubility of the compound will be a function of the length of the R carbon chain. However, one can also increase the solubility of the boron compounds by altering the $R_1$ and $R_2$ groups For example, compounds of formulae (II) and (III) herein before are soluble in 450 neutral oil, even when the R group side chain is relatively small. As an illustration, it is now known that a compound falling within formula (II), i.e., 1-hydroxy-3,7-diphenyl5-butyl-5-aza-1-bora-2,8-dioxacyclooctane, is known to be readily soluble in 450 neutral oil, despite the fact that the R group side chain is a relatively small butyl group. Thus, the relative solubility of boron compounds herein are dependent on both the length of the R group side chain and the length and nature of the $R_1$ and $R_2$ groups.

EXAMPLE 91

This Example compares the solubility and extreme pressure properties of boron compounds of the invention versus those disclosed in U.S. Pat. No. 3,227,739.

The procedure described in Example 1 of U.S. Pat. No. 3,227,739 was followed to prepare N,N-diethanol 2-hydroxy $C_{16}$–$C_{18}$ amine with the following exception:

Since the FMC Corporation no longer commercially produces the $C_{16}$–$C_{18}$ epoxide used, 1,2 epoxyoctadecane was substituted for the FMC epoxide. The reaction produced N,N-diethanol, 2-hydroxy $C_{18}$ amine.

The procedure described in Example 2 of U.S. Pat. No. 3,227,739 was followed to prepare the boric acid adduct of N,N-diethanol, 2-hydrox $C_{18}$ amine. The product thus produced (Compound A) was solid at room temperature.

Test No. 1

The boric acid adduct of N,N-diethanol, 2-hydroxy $C_{18}$ amine and the tallowaminodiethylate hydrogen borate (Compound B) produced in Example 2 hereinbefore were tested for oil solubility by adding the weight percentages indicated in Table 22 below to 450 neutral oil. The designated samples, including 450 neutral oil (100 grams total), were added to 250 ml Pyrex beakers equipped with teflon-coated, 30 magnetic stirring bars which had lengths of 2½ inches and diameters of ¼ inch. The Pyrex beakers were placed on Model PC-351 Corning hot plates and heated to the temperatures indicated in Table 22 with stirring (400 RPM of stirring bars) for ten minutes.

The Pyrex beakers were removed from the hot plates, and the 450 neutral oil mixtures were examined for oil solubility of the respective compounds in each sample. The results are summarized in the following Table 22:

TABLE 22

OIL SOLUBILITY CHART (450 Neutral Oil)

| COMPOUND | CONCENTRATION (wt %) | TEMPERATURE °F. (°C.) | SOLUBILITY AT 77° F. (25° C.) |
|---|---|---|---|
| 1. Compound A* | 0.5 | 260° F. (126.67° C.) | Cloudy, sediment |
| 2. Compound A | 1.0 | 260° F. (126.67° C.) | Cloudy, sediment |
| 3. Compound A | 2.0 | 260° F. (126.67° C.) | Cloudy, semi-gel |
| 4. Compound B** | 0.5 | 130° F. (54.44° C.) | Clear, soluble |
| 5. Compound B | 1.0 | 130° F. (54.44° C.) | Clear, soluble |

TABLE 22-continued

OIL SOLUBILITY CHART (450 Neutral Oil)

| COMPOUND | CONCENTRATION (wt %) | TEMPERATURE °F. (°C.) | SOLUBILITY AT 77° F. (25° C.) |
|---|---|---|---|
| 6. Compound B | 2.0 | 130° F. (54.44° C.) | Clear, soluble |

*Boric acid adduct of N,N—diethanol, 2-hydroxy $C_{18}$ amine prepared according to Examples 1 and 2 of U.S. Pat. No. 3,227,739.
**Tallowaminodiethylate hydrogen borate, where tallow = $C_{18}$ average.

Several temperatures were used in an attempt to fully dissolve Compound A, i.e., the boric acid adduct of N,N-diethanol, 2-hydroxyamine, in 450 neutral oil. At temperatures of 130° F. (54.44° C.), 200° F. (93.33° C.) and 225° F. (107.22° C.), the compound was insoluble in 450 neutral oil. The compound was soluble in 450 neutral oil at 260° F.(126.67° C.); however, upon cooling a cloudy appearance and sediment in the oil was noted. A concentration of 2 weight percent of Compound A produced a very viscous, semi-gel when mixed with 450 neutral oil and was unacceptable as an additive for the oil at this concentration.

Compound B, i.e., tallowaminediethylate hydrogen borate, was fully soluble in all samples tested at the standard 130° F. (54.44° C.) mixing temperature for oil additives and did not precipitate from the oil upon standing and cooling.

Test No. 2

The boric acid adduct of N,N-diethanol, 2-hydroxy $C_{18}$ amine and the tallowaminodiethylate hydrogen borate were also tested for oil solubility in the low phosphorus control SAE 30 motor oil (Example 47) in accordance with the procedure described above. The results are summarized in the following Table 23:

By comparison, Compound B was soluble in the SAE 30 motor oil in all samples tested at a temperature of 130° F. (54.44° C.). The compound remained in solution and did not form a precipitate or sediment in the oil upon standing.

Test No. 3

The boric acid adduct of N,N-diethanol, 2-hydroxy $C_{18}$ amine and tallowaminodiethylate hydrogen borate, both described above, were tested for extreme pressure properties in accordance with the procedure disclosed in ASTM:D 3233-73 (Reapproved 1978) using a Falex lubricant tester. The test, in accordance with the above ASTM designation, was performed by applying resistance (torque) to a revolving metal journal. A rachet mechanism movably attached to two V-blocks applied resistance by steadily increasing pressure on the journal. The metal journal and V-blocks, both constructed of steel, were submerged in the lubricant composition to be tested. The base oil in the experiments was the control SAE 30 motor oil (Example 47). The SAE 30 motor oil was chosen as the base oil because the boric acid adduct of N,N-diethanol, 2-hydrox $C_{18}$ amine was slightly more soluble in this oil and did not produce a semi-gel at higher concentrations as compared to 450

TABLE 23

OIL SOLUBILITY IN SAE 30 MOTOR OIL (EXAMPLE 47)

| COMPOUND | CONCENTRATION (wt %) | TEMPERATURE °F. (°C.) | SOLUBILITY AT 77° F. (25° C.) |
|---|---|---|---|
| 1. Compound A* | 0.5 | 260° F. (126.67° C.) | Hazy, slight sediment |
| 2. Compound A | 1.0 | 260° F. (126.67° C.) | Hazy, moderate sediment |
| 3. Compound A | 2.0 | 260° F. (126.67° C.) | Hazy, heavy sediment |
| 4. Compound B** | 0.5 | 130° F. (54.44° C.) | Clear, soluble |
| 5. Compound B | 1.0 | 130° F. (54.44° C.) | Clear, soluble |
| 6. Compound B | 2.0 | 130° F. (54.44° C.) | Clear, soluble |

*Boric acid adduct of N,N—diethanol, 2-hydroxy $C_{18}$ amine prepared according to Examples 1 and 2 of U.S. Pat. No. 3,227,739.
**Tallowaminodiethylate hydrogen borate, where tallow = $C_{18}$ average.

As shown in Table 23, Compound A was insoluble in the SAE 30 motor oil at all concentrations tested at temperatures of 130° F. (54.44° C. ), 200° F. (93.33° C.) and 225° F. (107.22° C.). At a temperature of 260° F. (126.67° C.), the compound did dissolve in the SAE 30 motor oil; however, upon standing, a sediment was noted in each sample.

neutral oil. However, this compound was not tested in the Falex lubricant tester at a concentration of 2 weight percent because at this concentration severe solubility problems were encountered in both the 450 neutral oil and the SAE 30 motor oil. The results are summarized in the following Table 24:

TABLE 24

| | TORQUE ON JOURNAL LBS.-IN. (NEWTON METERS) | | | |
|---|---|---|---|---|
| True Load lbs. (Newtons) | SAE 30 with 0.5 wt. % Compound A* | SAE 30 with 1.0 wt. % Compound A* | SAE 30 with 0.5 wt. % Compound B** | SAE 30 with 1.0 wt. % Compound B** |
| 300 (1,334) | 12 (1.356) | 12 (1.356) | 9 (1.017) | 10 (1.130) |
| 500 (2,224) | 20 (2.260) | 15 (1.695) | 12 (1.356) | 11 (1.243) |
| 700 (3,114) | Journal Shear | — | — | — |
| 750 (3,336) | | 20 (2.260) | 16 (1.808) | 14 (1.582) |
| 925 (4,114) | | — | — | — |
| 1,000 (4,448) | | 33 (3.729) | 20 (2.260) | 16 (1.808) |
| 1,050 (4,670) | | Journal Shear | — | — |
| 1,250 (5,560) | | | 24 (2.712) | 20 (2.260) |
| 1,350 (6,005) | | | Journal Shear | — |

TABLE 24-continued

| | TORQUE ON JOURNAL LBS.-IN. (NEWTON METERS) | | | |
|---|---|---|---|---|
| True Load lbs. (Newtons) | SAE 30 with 0.5 wt. % Compound A* | SAE 30 with 1.0 wt. % Compound A* | SAE 30 with 0.5 wt. % Compound B** | SAE 30 with 1.0 wt. % Compound B** |
| 1,450 (6,450) | | | | Journal Shear |

*Boric acid adduct of N,N—diethanol, 2-hydroxy $C_{18}$ amine.
**Tallowaminodiethylate hydrogen borate.

As shown in the foregoing Table 24, the compound prepared in accordance with the procedure of U.S. Pat. No. 3,227,739 had inferior extreme pressure properties when compared with Compound B prepared according to the procedure of Example 2 hereinbefore. In contrast, the data in Table 24 show that tallowaminodiethylate hydrogen borate exhibits superior extreme pressure properties when added to SAE 30 motor oil as compared to the boric acid adduct of N,N-diethanol, 2-hydrox $C_{18}$ amine. And based on the data in Tables 22 and 23 above, compounds of the type disclosed in U.S Pat. No. 3,227,739 experience oil solubility problems in 450 neutral oil and SAE 30 motor oil at concentrations of 0.5, 1.0, and 2.0 weight percent. In contrast, the tallowaminodiethylate hydrogen borate is completely soluble at such concentrations.

EXAMPLE 92

This example compares the solubility and extreme pressure properties of a compound disclosed in U.S. Pat. No. 3,224,971 against the boron compounds produced according to Examples 1 and 2 hereinbefore.

The tris (borate ester) of bis (o-hydroxy-octylphenylmethyl) amine was prepared in accordance with the procedure in Example 3 (column 3, lines 39 to 69) of U.S. Pat. No. 3,224,971.

The borate ester was prepared by mixing 205 grams of 5-octylphenol, 23.4 grams of hexamethylenetetramine and 500 ml of toluene in a single-necked one-liter round-bottomed flask. The flask was placed in a heating mantle and fitted with a Dean-Stark trap and water-cooled condenser. The mixture was refluxed for 24 hours. Next, 20.6 grams of boric acid were added to the flask and the mixture was refluxed for an additional four hours during which water produced in the reaction was collected in the Dean-Stark trap.

Test No. 1

An experiment was performed to compare the boron compounds of Examples 1 and 2 hereinbefore with the borate ester described above in the Ryder Gear Test disclosed in column 6, lines 1 to 48 and Table 6 of U.S. Pat. No. 3,224,971. The base oil used in the test was di-2-ethyl-hexyl sebacate.

A one-gram sample of the boron compound of Example 1 hereinbefore was admixed with 99 grams of di-2-ethyl-hexyl sebacate at 120° F. (48.89° C.) in a 250-ml Pyrex glass beaker. The boron compound did not dissolve in the base oil. The mixture formed was cloudy and the boron compound settled to the bottom of the beaker upon standing. The mixture was heated to 300° F. (148.89° C.); however, the boron compound did not dissolve in the di-2-ethyl-hexyl sebacate.

Next, a one-gram sample of the boron compound of Example 2 hereinbefore was admixed with 99 grams of di-2-ethyl-hexyl sebacate at 120° F. (48.89° C.) in a 200-ml Pyrex glass beaker. This boron compound did not dissolve in the base oil. The base oil and boron compound mixture was heated to 300° F. (148.89° C.), but the boron compound still did not dissolve in the base oil.

Additional experiments to determine the effectiveness of the two boron compounds as extreme pressure agents in the Ryder Gear Test were not conducted, because the compounds would not go into solution in the di-2-ethylhexyl sebacate base oil. However, experiments were conducted to compare the effectiveness in an SAE 10W 40 motor oil of these compounds and the tris borate esters of U.S. Pat. No. 3,224,971 as extreme pressure agents in a Falex lubricant tester.

Test No. 2

The boron compounds of Examples 1 and 2 and the tris (borate ester) of bis (o-hydroxy-octylphenylmethyl) amine described above were tested in accordance with the procedure disclosed in ASTM D3233-73 (Reapproved 1978) using a Falex lubricant tester. The test was performed by applying resistance to a revolving metal journal. A rachet mechanism movably attached to two V-blocks applied resistance by steadily increasing pressure on the journal. The metal journal and V-blocks, both constructed of steel, were submerged in the lubricant composition to be tested. The base oil in the experiments was an SAE 10W/40 motor oil marketed commercially by the Union Oil Company of California. The results are summarized in the following Table 25:

TABLE 25

| Composition | Highest Jaw Load Before Failure, Lbs. (Newtons) |
|---|---|
| (1) SAE 10W/40 oil without any additive | 1,400 (6,227) |
| (2) SAE 10W/40 oil plus 1.0 wt. % Example 1 compound | 1,700 (7,562) |
| (3) SAE 10W/40 oil plus 1.0 wt. % Example 2 compound | 2,250 (10,008) |
| (4) SAE 10W/40 oil plus 1.0 wt. % tris borate ester of bis (o-hydroxy-octylphenylmethyl) amine | 900 (4,003) |
| (5) SAE 10W/40 oil plus 2.0 wt. % tris borate ester of bis (o-hydroxy-octylphenylmethyl) amine | 900 (4,003) |

As shown in Table 25 above, the Example 1 and 2 compounds substantially increased the load carrying property (extreme pressure property) of SAE 10W/40 base oil in the Falex lubricant tester, while bis (o-hydroxyoctylphenylmethyl) amine had a detrimental effect upon the base oil, reducing the load carrying property of said oil by 500 pounds. The amount of bis (o-hydroxy-octylphenylmethyl) amine added to the base oil was doubled with the same detrimental effect noted.

Test No. 3

The boron compound of Example 1 hereinbefore and the tris (borate ester) of bis (o-hydroxy-octylphenylmethyl) amine described above were tested in accordance with the procedure of Test No. 2 with the following exception: 450 neutral oil marketed by the Union Oil Company of California was substituted for the SAE 10W/40 oil. The results are summarized in the following Table 26:

TABLE 26

| Composition | Highest Jaw Load Before Failure, Lbs. (Newtons) |
|---|---|
| (1) 450 neutral without additive | 700 (3,114) |
| (2) 450 neutral oil plus 1.0 wt. % Example 1 compound | 1,100 (4,893) |
| (3) 450 neutral oil plus 1.0 wt. % tris borate ester of bis (o-hydroxy-octylphenylmethyl) amine | 700 (3,114) |
| (4) 450 neutral oil plus 5.0 wt. % tris borate ester of bis (o-hydroxy-octylphenylmethyl) amine | 700 (3,114) |

As shown in Table 26 above, the boron compound of Example 1 increased the load carrying property (extreme pressure) of 450 neutral base oil in the Falex lubricant tester. Bis (o-hydroxyoctylphenylmethyl) amine did not affect the base oil either positively or negatively; the load-carrying property of the base oil was the same with or without the additive.

EXAMPLE 93

The combination of a solution of an oil-soluble copper carboxylate such as copper naphthenate and a boron-containing heterocyclic compound both sulfurized and nonsulfurized gives better anti-wear protection in an oil than either component separately.

In the four-ball wear test (40 kg., 600 rpm, 167° F. (75° C.), 1 hour (ASTM D 4172-82 modified to run at 600 rpm)), one loaded steel ball rotates against three stationary balls. The average wear scar diameter of the three stationary balls is a measure of wear. The reported wear scar diameters are the average scar diameters minus the Hertz scar diameter (the average diameter in millimeters of an indentation caused by the deformation of the balls under static load, calculated from $D_h = 8.73 \times 10^{-2}(P)^{\frac{1}{3}}$ where $D_h$ is the Hertz diameter of the contact area, and P is the static applied load).

The four-ball wear test was performed on an automotive oil (450 neutral) containing the ingredients indicated in Table 27, with the results of the tests also being indicated therein. The borates of the invention all give better wear protection than copper naphthenate. However, a combination of copper naphthenate solution and borates solution gives significantly better wear protection than either component alone. Therefore, there is a synergistic interaction between copper naphthenate and the borates of the invention.

TABLE 27

EFFECT OF COPPER PLUS BORATES ON ANTI-WEAR PERFORMANCE

| Cu Naphthenate conc., wt. % | Borate (I)[1] conc., wt. % | Borate (II)[2] conc., wt. % | Borate (III)[3] conc., wt. % | Scar Diameter, mm[4] |
|---|---|---|---|---|
| 2.0 | — | — | — | 0.22 |
| — | 1.5 | — | — | 0.18 |
| — | — | 2.0 | — | 0.15 |

TABLE 27-continued

EFFECT OF COPPER PLUS BORATES ON ANTI-WEAR PERFORMANCE

| Cu Naphthenate conc., wt. % | Borate (I)[1] conc., wt. % | Borate (II)[2] conc., wt. % | Borate (III)[3] conc., wt. % | Scar Diameter, mm[4] |
|---|---|---|---|---|
| — | — | — | 2.0 | 0.18 |
| 1.0 | 0.75 | — | — | 0.10 |
| 1.0 | — | 1.0 | — | 0.12 |
| 1.0 | — | — | 1.0 | 0.06 |

[1]Borate (I) is a sulfurized 1-hydroxy-3,7-diphenyl-5-tallow-5-aza-1-bora-2,8-dioxacyclooctane.
[2]Borate (II) is 1-(2,6-di-tert-butyl-4-methylphenoxy)-3,7-dimethyl-5-tallow-5-aza-1-bora-2,8-dioxacyclooctane.
[3]Borate (III) is a sulfurized Borate (II).
[4]Average scar diameter minus Hertz scar diameter.

EXAMPLE 94

Tallowamine (distilled) from Armak Chemical Company (94.04 grams, 0.36 mole ), styrene oxide from Union Carbide (94.21 grams, 0.70 moles) and toluene (200 ml) were stirred at room temperature for 30 minutes in a round-bottomed flask equipped with a reflux condenser. The mixture (solution) was heated to the reflux temperature of toluene for three hours producing an amine:styrene oxide adduct. The adduct was cooled in the flask to room temperature (25° to 30° C.) and boric acid (21.75 gram, 0.35 mole) was added. A Dean Stark-type water separation apparatus was inserted between the flask and condenser. After 12.5 ml of water was collected in the Dean Stark sidearm, the reaction was presumed to be over. The flask and contents were then moved to a rotary evaporator to strip off the toluene leaving the product, 1-hydroxy-3,7-diphenyl-5-tallow-5-aza-1-bora-2,8-dioxacyclooctane. This borate of the invention (75 g) and 100 ml of toluene are refluxed in a round-bottomed flask. 2.2 g of sulfur is added to the refluxing mixture. The solution continued to reflux for 4 hours, then cooled to room temperature where 25 g of 450 neutral oil is added and the toluene is eliminated by rotary evaporation. The product is a brown, viscous sticky oil, i.e., a sulfurized form of 1-hydroxy-3,7-diphenyl-5-tallow-5-aza-1-bora-2,8-dioxacyclooctane.

This patent application incorporates by reference the following U.S. patents and patent applications in their entireties: U.S. Pat. Nos. 4,400,284, 4,410,436, 4,412 928, 4,427,560, 4,490,265, U.S. patent application Ser. No. 158,981 filed June 12, 1980, U.S. patent application Ser. No. 329,385 filed December 10, 1981, U.S. patent application Ser. No. 418,196 filed Sept. 15, 1982, U.S. patent application Ser. No. 476,513 filed Mar. 18, 1983, U.S. patent application Ser. No. 525,691 filed Aug.23, 1983, U.S. patent application Ser. No. 525,718 filed Aug. 23, 1983, U.S. patent application Ser. No. 525,719 filed Aug. 23, 1983, U.S. patent application Ser. No. 525,720 filed Aug. 23, 1983, and U.S. patent application Ser. No. 679,286 filed Dec. 7, 1984.

Obviously, many modifications and variations of this invention, as hereinbefore set forth, may be made without departing from the spirit and scope thereof. For example, although the specification focused on the preferred embodiment relating to oils for use in gasoline-powered automotive engines, the borates of the invention are useful in lubricating oils for diesel engines. In fact, it has been discovered that the borates of the invention, and especially the sulfurized version of 1-hydroxy-3,7-diphenyl-5-tallow-5-aza-1-bora-2,8-dioxacyclooctane, the most preferred borate of the present invention, markedly reduce and/or prevent the formation of deposits in the upper ring zone of diesel engines, such as the Caterpillar 1-H2 Diesel Engine. Thus, it is intended that this embodiment of the invention and other such modifications and variations falling within the spirit and scope of the appended claims are embraced within the present invention.

I claim:

1. A lubrication composition comprising a lubricating oil containing an antiwear enhancing amount of a dissolved copper carboxylate and a boron-containing compound of the formula

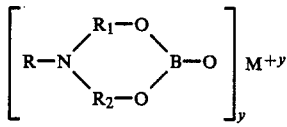

wherein:
y is an integer;
M is a inorganic or organic radical;
R is a $C_1$ to $C_{50}$ organic radical; and
$R_1$ and $R_2$ are the same or different $C_1$ to $C_{50}$ organic radical.

2. The composition of claim 1 wherein the copper compound is copper naphthenate.

3. The composition of claim 1 wherein M is a metal.

4. The composition of claim 2 wherein M is a Periodic Group IB, IIB, IIIB, IVB, VB, VIB, VIIB, VIII, IIIA, IVA, OR VA metal.

5. The composition of claim 1 wherein M is $C_1$ to $C_{50}$ organic radical.

6. The composition of claim 5 wherein M is derived from an aliphatic, alicyclic, or aromatic compound.

7. The composition of claim 1 wherein M is hydrogen.

8. A lubrication composition comprising a lubricating oil, at least about 100 wppm of a dissolved copper carboxyate, as measured by the concentration of copper present in the composition, and from about 0.1 to 15 weight percent of a boron-containing compound of the formula:

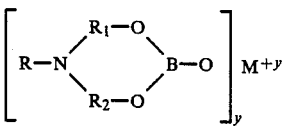

wherein: y is an integer;
M is an inorganic or organic radical;
R is a $C_1$ to $C_{50}$ organic radical; and
$R_1$ and $R_2$ are the same or different $C_1$ to $C_{50}$ organic radical.

9. The composition of claim 8 wherein the copper compound is no more than about three weight percent of the composition.

10. The composition of claim 8 wherein the copper compound is from about 100 wppm to about 125 wppm of the composition.

11. The composition of claim 9 wherein M is a Periodic Group IB, IIB, IIIB, IVB, VB, VIB, VIIB, VIII, IIIA, IVA, or VA metal.

12. The composition of claim 9 wherein M is a transition metal having an atomic number of 21 to 30 or a Group IVA meta.

13. The composition of claim 9 wherein M is copper.

14. The composition of claim 3, 4, 1, or 12 wherein y is an integer from 1 to 4.

15. The composition of claim 9 wherein M is a $C_1$ to $C_{50}$ substituted or unsubstituted alkyl, alkenyl, alkynyl, aryl, alkylaryl, or arylalkyl radical.

16. The composition of claim 9 wherein M is a methyl or cyclohexyl radical.

17. The composition of claim 9 wherein M is hydrogen.

18. The composition of claim 14 wherein R is a $C_1$ to $C_{30}$ organic radical.

19. The composition of claims 6, 15, or 17 wherein R is a $C_1$ to $C_{30}$ organic radical.

20. The composition of claim 18 wherein R is a substituted or unsubstituted alkyl, alkenyl, alkynyl, aryl, arylalkyl, or alkylaryl radical.

21. The composition of claim 17 wherein R is a substituted or unsubstituted alkyl, alkenyl, alkynyl, aryl, arylalkyl, or alkylaryl radical.

22. The composition of claim 18 wherein R is a $C_9$ to $C_{20}$ radical.

23. The composition of claim 19 wherein R is a $C_9$ to $C_{20}$ radical.

24. The composition of claim 14 wherein R is of the formula:

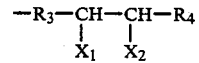

wherein:
$R_3$ is a $C_1$ to $C_{30}$ organic radical;
$R_4$ is an inorganic or $C_1$ to $C_{30}$ organic radical;
$X_1$ is a halogen; and
$X_2$ is a halogen or a sulfide bridge between two organic radicals of the boron-containing heterocyclic compound or connecting another boron-containing heterocyclic compound of the same type.

25. The composition of claims 6, 15, or 17 wherein R is of the formula:

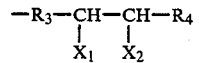

wherein:
$R_3$ is a $C_1$ to $C_{30}$ organic radical;
$R_4$ is an inorganic or $C_1$ to $C_{30}$ organic radical;
$X_1$ is a halogen; and
$X_2$ is a halogen or a sulfide bridge between two organic radicals of the boron-containing heterocyclic compound or connecting another boron-containing heterocyclic compound of the same type.

26. The composition of claim 18 wherein $R_1$ and $R_2$ are the same or different $C_2$ to $C_{30}$ organic radical.

27. The composition of claim 19 where in $R_1$ and $R_2$ are the same or different $C_2$ to $C_{30}$ organic radical.

28. The composition of claim 20 wherein $R_1$ and $R_2$ are the same or different $C_2$ to $C_{30}$ organic radical.

29. The composition of claim 21 wherein $R_1$ and $R_2$ are the same or different $C_2$ to $C_{30}$ organic radical.

30. The composition of claim 25 wherein $R_1$ and $R_2$ are the same or different $C_2$ to $C_{30}$ organic radical.

31. The compound of claim 26 wherein $R_1$ and $R_2$ are the same or different substituted or unsubstituted alkyl, aryl, alkenyl, alkynyl, alkylaryl, or arylalkyl radical.

32. The compound of claim 27 wherein $R_1$ and $R_2$ are the same or different substituted or unsubstituted alkyl, aryl, alkenyl, alkynyl, alkylaryl, or arylalkyl radical.

33. The compound of claim 28 wherein $R_1$ and $R_2$ are the same or different substituted or unsubstituted alkyl, aryl, alkynyl, alkylaryl, or arylalkyl radical.

34. The compound of claim 29 wherein $R_1$ and $R_2$ are the same or different substituted or unsubstituted alkyl, aryl, alkenyl, alkynyl, alkyaryl, or arylalkyl radical.

35. The compound of claim 30 wherein $R_1$ and $R_2$ are the same or different substituted or unsubstituted alkyl, aryl, alkenyl, alkynyl, alkylaryl, or arylalkyl radical.

36. The composition of claim 18 wherein $R_1$ and $R_2$ are the same or different radical of the formula:

$$-\underset{\underset{R_7}{|}}{\overset{\overset{R_5}{|}}{C}}-\underset{\underset{R_8}{|}}{\overset{\overset{R_6}{|}}{C}}-$$

wherein: $R_5$, $R_6$, $R_7$, and $R_8$ are the same or different and are hydrogen or an organic radical, provided that at least one of $R_5$ and $R_6$ is a $C_6$ to $C_{30}$ aryl, alkylaryl, or arylalkyl radical.

37. The composition of claim 19 wherein $R_1$ and $R_2$ are the same or different radical of the formula:

$$-\underset{\underset{R_7}{|}}{\overset{\overset{R_5}{|}}{C}}-\underset{\underset{R_8}{|}}{\overset{\overset{R_6}{|}}{C}}-$$

wherein: $R_5$, $R_6$, $R_7$, and $R_8$ are the same or different and are hydrogen or an organic radical, provided that at least one of $R_5$ and $R_6$ is a $C_6$ to $C_{30}$ aryl, alkylaryl, or arylalkyl radical.

38. The composition of claim 23 wherein $R_1$ and $R_1$ are the same or different radical of the formula:

$$-\underset{\underset{R_7}{|}}{\overset{\overset{R_5}{|}}{C}}-\underset{\underset{R_8}{|}}{\overset{\overset{R_6}{|}}{C}}-$$

wherein: $R_5$, $R_6$, $R_7$, and $R_8$ are the same or different and are hydrogen or an organic radical, provided that at least one of $R_5$ and $R_6$ is a $C_6$ to $C_{30}$ aryl, alkylaryl, or arylalkyl radical.

39. The composition of claim 33 wherein the boron-containing heterocyclic compound is from about 0.1 to about 15 weight percent of the composition.

40. The composition of claim 36 wherein the boron-containing heterocyclic compound is from about 0.1 to about 15 weight percent of the composition.

41. The composition of claim 37 wherein the boron-containing heterocyclic compound is from about 0.1 to about 15 weight percent of the composition.

42. The lubrication composition of claim 39 further comprising a minor proportion of at least one additive selected from the group consisting of:

(I) a compound of the formula $$R_{46}-(S)_w-\underset{S}{\overset{\overset{N=\!\!=\!\!=N}{||\quad\quad||}}{C\quad\quad C}}-(S)_z-R_{47}$$

wherein $R_{46}$ and $R_{47}$ are moieties selected from hydrogen or straight or branched chain alkyl, cyclic or alicyclic alkyl, aryl, alkylaryl or arylalkyl radicals having from 2 to about 30 carbon atoms, provided that $R_{46}$ and $R_{47}$ are not both hydrogen and w and z are numbers from 1 to about 8;

(II) terephthalic acid;

(III) a compound of the formula:

$$\left[\bigcirc\!\!-\!\!\overset{\overset{S}{||}}{C}\!\!-\!\!\underset{\underset{H}{|}}{\overset{\overset{S^-}{|}}{C}}\!\!-\!\!\bigcirc\right]_t M_{10}^{+t}$$

wherein $M_{10}$ is a first row transition metal and t is an integer from 1 to 4;

(IV) a compound of the formula:

$$\left[HO-\underset{\underset{R_{49}}{}}{\overset{\overset{R_{48}}{}}{\bigcirc}}-(CH_2)_2-\overset{\overset{O}{||}}{C}-O-(CH_2)_2-\right]_2 S$$

wherein $R_{48}$ and $R_{49}$ are the same or different alkyl radical having from 1 to 6 carbon atoms; and (V) a compound of the formula:

$$R_{52}-\underset{H}{\overset{\overset{}{|}}{N}}-R_{53}$$

wherein $R_{52}$ and $R_{53}$ are hydrogen or the same or different alkyl radical having from 1 to about 30 carbon atoms.

43. The lubrication composition of claim 40 further comprising a minor proportion of at least one additive selected from the group consisting of:

(I) a compound of the formula:

$$R_{46}-(S)_w-\underset{S}{\overset{\overset{N=\!\!=\!\!=N}{||\quad\quad||}}{C\quad\quad C}}-(S)_z-R_{47}$$

wherein $R_{46}$ and $R_{47}$ are moieties selected from hydrogen or straight or branched chain alkyl, cyclic or alicyclic alkyl, aryl, alkylaryl or arylalkyl radicals having from 2 to about 30 carbon atoms, provided that $R_{46}$ and $R_{47}$ are not both hydrogen and w and z are numbers from 1 to about 8;

(II) terephthalic acid;

(III) a compound of the formula:

$$\left[\bigcirc\!\!-\!\!\overset{\overset{S}{||}}{C}\!\!-\!\!\underset{\underset{H}{|}}{\overset{\overset{S^-}{|}}{C}}\!\!-\!\!\bigcirc\right]_t M_{10}^{+t}$$

wherein $M_{10}$ is a first row transition metal and t is an integer from 1 to 4;

(IV) a compound of the formula:

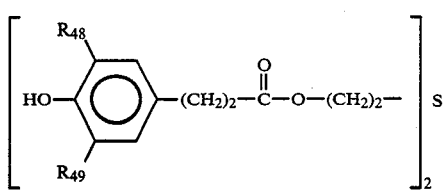

wherein $R_{48}$ and $R_{49}$ are selected from the same or different alkyl groups having from 1 to 6 carbon atoms; and (V) a compound of the formula:

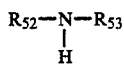

wherein $R_{52}$ and $R_{53}$ are hydrogen or the same or different alkyl radical having from 1 to about 30 carbon atoms.

44. The lubrication composition of claim 41 further comprising a minor proportion of at least one additive selected from the group consisting of:

(I) a compound of the formula:

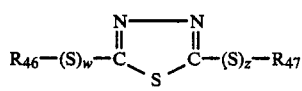

wherein $R_{46}$ and $R_{47}$ are moieties selected from hydrogen or straight or branched chain alkyl, cyclic or alicyclic alkyl, aryl, alkylaryl or arylalkyl radicals having from 2 to about 30 carbon atoms, provided that $R_{46}$ and $R_{47}$ are not both hydrogen and w and z are numbers from 1 to about 8;

(II) terephthalic acid;

(III) a compound of the formula:

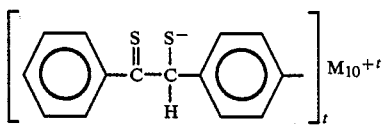

wherein $M_{10}$ is a first row transition metal and t is an integer from 1 to 4;

(IV) a compound of the formula:

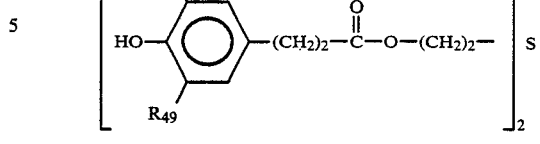

wherein $R_{48}$ and $R_{49}$ are selected from the same or different alkyl groups having from 1 to 6 carbon atoms; and (v) a compound of the formula

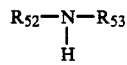

wherein $R_{52}$ and $R_{53}$ are hydrogen or the same or different alkyl radical having from 1 to about 30 carbon atoms.

45. The composition of claim 9, 10, 12, 15, or 17 wherein said copper compound comprises copper naphthenate.

46. The composition of claim 45 wherein R is a substituted or unsubstituted alkyl, alkenyl, alkynyl, aryl, arylalkyl, or alkylaryl radical.

47. The composition of claim 46 wherein R is a $C_9$ to $C_{20}$ radical.

48. The composition of claim 45 wherein R comprises sulfur.

49. The composition of claim 45 wherein $R_1$ and $R_2$ are the same or different radical of the formula:

wherein: $R_5$, $R_6$, $R_7$, and $R_8$ are the same or different and are hydrogen or an organic radical, provided that at least One Of $R_5$ and $R_6$ is a $C_6$ to $C_{30}$ aryl, alkyaryl, or arylalkyl radical.

50. The composition of claim 1, 2, 8, or 9 wherein M is selected from the group consisting of $C_1$ to $C_{50}$ organic radicals, hydrogen, and the metals or the Periodic Groups IIB, IIIB, IVB, VB, VIB, VIIB, VIII, IIA, IVA, or VA.

51. The composition of claim 1, 3, 5, 6, 7, 8, 9, 10, 11, 12, 13, 15, 16, or 17 wherein R, $R_1$, or $R_2$ comprises sulfur.

52. The composition of claim 51 wherein said copper compound is copper naphthenate.

53. The composition of claim 51 wherein said copper compound is a copper carboxylate.

* * * * *

UNITED STATES PATENT AND TRADEMARK OFFICE
CERTIFICATE OF CORRECTION

PATENT NO. : 4,892,670

DATED : January 9, 1990

INVENTOR(S) : Leah T. Mendelson

Page 1 of 2

It is certified that error appears in the above-identified patent and that said Letters Patent is hereby corrected as shown below:

The title page, showing the number of claims in patent should be deleted and substituted therefore the attached title page.

Column 55, line 68, change "meta" to --metal--.
Column 56, line 2, change "1" to --11--.
Column 56, line 18, change "17" to --19--.
Column 56, line 21, change "18" to --20--.
Column 56, line 23, change "19" to --21--.
Column 60, line 43, change "One Of" to --one of--.
Column 60, line 48, change "IIA" to --IIIA--.
Column 60, lines 55 and 56, delete this claim.

Signed and Sealed this

Twenty-seventh Day of April, 1993

*Attest:*

MICHAEL K. KIRK

*Attesting Officer*  *Acting Commissioner of Patents and Trademarks*

United States Patent [19]

Mendelson

[11] Patent Number: 4,892,670

[45] Date of Patent: Jan. 9, 1990

[54] LUBRICATING COMPOSITIONS

[75] Inventor: Leah T. Mendelson, Santa Ana, Calif.

[73] Assignee: Union Oil Company of California, Los Angeles, Calif.

[21] Appl. No.: 695,958

[22] Filed: Jan. 29, 1985

[51] Int. Cl.[4] .................................................. C10M 141/02
[52] U.S. Cl. ................................... 252/37; 252/42.7; 252/46.4; 252/49.6; 252/56 R; 252/49.7
[58] Field of Search ................ 252/49.7, 42, 37, 42.7, 252/46.4, 49.6, 56 R, 47

[56] References Cited

U.S. PATENT DOCUMENTS

| | | | |
|---|---|---|---|
| 2,234,581 | 3/1941 | Rosen | 252/51 |
| 2,441,063 | 5/1948 | Gilmann | 260/404 |
| 2,999,064 | 9/1961 | Sluham | 252/34.7 |
| 3,000,925 | 9/1961 | Rudner et al. | 260/462 |
| 3,011,880 | 12/1961 | Liao et al. | 44/63 |
| 3,011,881 | 12/1961 | Emrick et al. | 44/63 |
| 3,030,405 | 4/1962 | Rudner et al. | 260/462 |
| 3,185,644 | 5/1965 | Knowles et al. | 252/33.6 |
| 3,186,946 | 6/1965 | Sluhan | 252/49.3 |
| 3,224,971 | 12/1965 | Knowles et al. | 252/46.3 |
| 3,227,739 | 1/1966 | Versteeg | 260/462 |
| 3,232,875 | 2/1966 | Abend | 252/49.6 |
| 3,256,310 | 6/1966 | Weil | 252/462 |
| 3,269,853 | 8/1966 | English et al. | 106/243 |
| 3,285,855 | 11/1966 | Dexter et al. | 252/57 |
| 3,313,727 | 4/1967 | Peeler | 252/18 |
| 3,321,506 | 5/1967 | Knowles et al. | 260/462 |
| 3,429,909 | 2/1969 | Schuster | 260/462 |
| 3,598,757 | 8/1971 | Cyba | 252/400 |
| 3,598,855 | 8/1971 | Cyba | 260/462 R |
| 3,642,652 | 2/1972 | Birgy | 252/389 |
| 3,692,681 | 9/1972 | Liston | 252/51.5 A |
| 3,697,574 | 10/1972 | Piasek et al. | 260/462 R |
| 3,755,388 | 8/1973 | Ludwig et al. | 260/404 |
| 3,764,593 | 10/1973 | Schuster | 260/97.5 |
| 3,912,643 | 10/1975 | Adams | 252/49.6 |
| 3,912,644 | 10/1975 | Adams | 252/49.6 |
| 3,929,652 | 12/1975 | Seni et al. | 252/46.7 |
| 3,977,986 | 8/1976 | Conte, Jr. et al. | 252/78.3 |
| 4,025,445 | 5/1977 | Hellmuth et al. | 252/49.6 |
| 4,032,304 | 6/1977 | Dorer, Jr. et al. | 44/70 |
| 4,115,286 | 9/1978 | Baldwin et al. | 252/46.3 |
| 4,136,039 | 1/1979 | Jager et al. | 252/8.8 |
| 4,176,076 | 11/1979 | Waldstein | 252/49.6 |
| 4,204,972 | 5/1980 | Knoblauch et al. | 252/78.1 |
| 4,226,734 | 10/1980 | Schuster | 252/49.3 |
| 4,234,435 | 11/1980 | Meinhardt et al. | 252/51.5 |
| 4,382,006 | 5/1983 | Horodysky | 252/49.6 |
| 4,400,284 | 8/1983 | Jessup et al. | 252/49.6 |
| 4,406,802 | 9/1983 | Horodysky et al. | 252/49.6 |
| 4,410,436 | 10/1983 | Holstedt et al. | 252/49.6 |
| 4,410,438 | 10/1983 | Horodysky | 252/49.6 |
| 4,412,928 | 11/1983 | Holstedt et al. | 252/49.6 |
| 4,427,560 | 1/1984 | Holstedt et al. | 252/49.7 |
| 4,431,552 | 2/1984 | Salentine | 252/46.7 |
| 4,474,670 | 10/1984 | Braid et al. | 252/32.7 |
| 4,478,732 | 10/1984 | Horodysky et al. | 252/49.6 |
| 4,490,265 | 12/1984 | Holstedt et al. | 252/49.7 |
| 4,492,640 | 1/1985 | Horodysky et al. | 252/46.3 |
| 4,492,642 | 1/1985 | Horodysky | 252/49.6 |
| 4,497,719 | 2/1985 | King et al. | 252/37 |
| 4,511,516 | 4/1985 | Holstedt et al. | 252/49.6 |
| 4,531,948 | 7/1985 | Knapp | 44/53 |
| 4,533,480 | 8/1985 | Holstedt et al. | 252/49.7 |
| 4,549,975 | 10/1985 | Horodysky | 252/49.6 |
| 4,557,843 | 12/1985 | Holstedt et al. | 252/46.4 |

FOREIGN PATENT DOCUMENTS

| | | |
|---|---|---|
| 1306233 | 2/1973 | United Kingdom . |
| 1520743 | 8/1978 | United Kingdom . |
| 2177418A | 1/1987 | United Kingdom . |

*Primary Examiner*—Jacqueline V. Howard
*Attorney, Agent, or Firm*—Gregory F. Wirzbicki; Michael C. Schiffer

[57] ABSTRACT

A boron-containing heterocyclic compound prepared by reacting a primary amine or ammonia with an alkylene oxide or epoxide and then reacting concurrently or subsequently this reaction intermediate with a boric acid. This boron-containing heterocyclic compound may further be reacted with a metal, metaloid or other metal compound and even further contain sulfur, such as a sulfide group.

The boron-containing heterocyclic compound provides extreme pressure anti-wear properties when provided in a lubricating composition. The lubricating composition may also comprise anti-oxidants, copper corrosion inhibitors, and lead corrosion inhibitors. The anti-wear properties of a lubricating composition can be enhanced using the borates of the present invention in conjunction with a copper compound.

52 Claims, No Drawings